US009835619B2

(12) United States Patent
Akagami et al.

(10) Patent No.: US 9,835,619 B2
(45) Date of Patent: Dec. 5, 2017

(54) APPARATUS FOR AUTOMATIC ELECTRIC FIELD IMMUNOHISTOCHEMICAL STAINING AND METHOD FOR AUTOMATIC ELECTRIC FIELD IMMUNOHISTOCHEMICAL STAINING

(71) Applicants: GOVERNOR OF AKITA PREFECTURE, Akita-shi, Akita (JP); AKITA UNIVERSITY, Akita-shi, Akita (JP)

(72) Inventors: Yoichi Akagami, Akita (JP); Masami Kagaya, Akita (JP); Ryuta Nakamura, Akita (JP); Hiroshi Ikeda, Akita (JP); Yoshihiro Minamiya, Akita (JP); Hiroshi Nanjo, Akita (JP)

(73) Assignees: Governor of Akita Prefecture, Akita-shi, Akita (JP); Akita University, Akita-shi, Akita (JP)

( * ) Notice: Subject to any disclaimer, the term of this patent is extended or adjusted under 35 U.S.C. 154(b) by 725 days.

(21) Appl. No.: 14/185,533

(22) Filed: Feb. 20, 2014

(65) Prior Publication Data
US 2015/0233902 A1    Aug. 20, 2015

(51) Int. Cl.
*G01N 1/31* (2006.01)
*G01N 33/53* (2006.01)
(Continued)

(52) U.S. Cl.
CPC ............ *G01N 33/5302* (2013.01); *B01L 9/52* (2013.01); *G01N 1/28* (2013.01); *G01N 1/30* (2013.01);
(Continued)

(58) Field of Classification Search
CPC G01N 1/312; G01N 1/28; G01N 1/30; G01N 35/00029; G01N 33/5302;
(Continued)

(56) References Cited

U.S. PATENT DOCUMENTS

| 2010/0028978 A1* | 2/2010 | Angros ................. B01L 3/0293 435/283.1 |
| 2012/0003669 A1* | 1/2012 | Minamiya ................ G01N 1/30 435/7.9 |

FOREIGN PATENT DOCUMENTS

| JP | 4-507295 A | 12/1992 |
| JP | 2008-527330 A | 7/2008 |

(Continued)

OTHER PUBLICATIONS

Nakamura et al., "Investigation of the mechanism for rapid antigen-antibody reaction using noncontact stirring method under high voltage AC electric field", JSPE, 2013, 3 total pages.

*Primary Examiner* — Erik B Crawford
(74) *Attorney, Agent, or Firm* — Sughrue Mion, PLLC

(57) ABSTRACT

Acceleration and automation of immunohistochemical staining are achieved as follows: an automatic electric field immunohistochemical staining apparatus is configured to provided with a sample mounting unit, a solution supply unit, an electric field stifling unit, and a washing unit; the sample mounting unit on which a glass substrate with a tissue specimen fixed thereto is mounted and the electric field stirring unit that includes an upper electrode are operated in coordination to activate an antigen in the tissue specimen; the sample mounting unit and the solution supply unit containing various solutions are operated in coordination to supply a primary-antibody-containing solution to the tissue specimen; the sample mounting unit and the electric field stirring unit are operated in coordination to perform an antigen-antibody reaction of the antigen in the tissue specimen and a primary antibody; and the electric field stirring unit and the washing unit are operated in coordination.

24 Claims, 14 Drawing Sheets

(51) Int. Cl.
*B01L 9/00* (2006.01)
*G01N 35/00* (2006.01)
*G01N 1/28* (2006.01)
*G01N 1/30* (2006.01)

(52) U.S. Cl.
CPC ....... *G01N 1/312* (2013.01); *G01N 35/00029* (2013.01); *B01J 2219/00364* (2013.01); *B01J 2219/00371* (2013.01); *G01N 2001/317* (2013.01)

(58) Field of Classification Search
CPC ................. G01N 2001/317; B01L 9/52; B01L 2219/00364; B01L 2219/00371
USPC ..... 422/224, 536; 435/40.5; 436/43, 46, 174
See application file for complete search history.

(56) References Cited

FOREIGN PATENT DOCUMENTS

| | | |
|---|---|---|
| JP | 2010-119388 A | 6/2010 |
| JP | 2012-013598 A | 1/2012 |
| JP | 2012-159480 A | 8/2012 |
| WO | 91/02962 A1 | 3/1991 |
| WO | 2006/073910 A2 | 7/2006 |

\* cited by examiner

FIG. 9
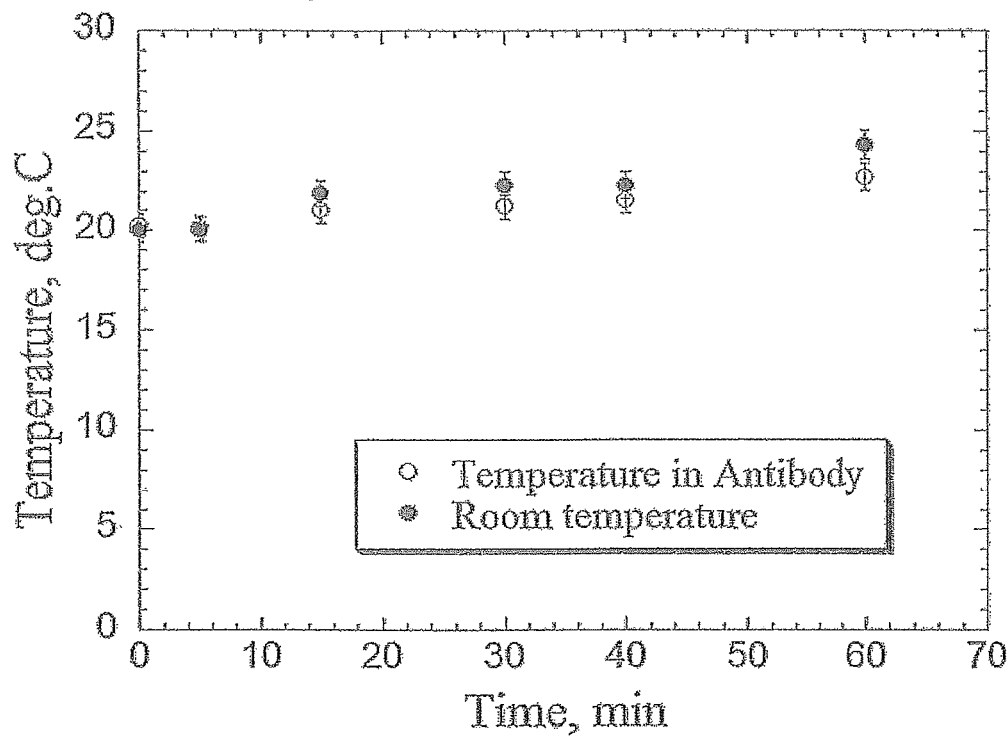
AT A FREQUENCY OF 21 Hz
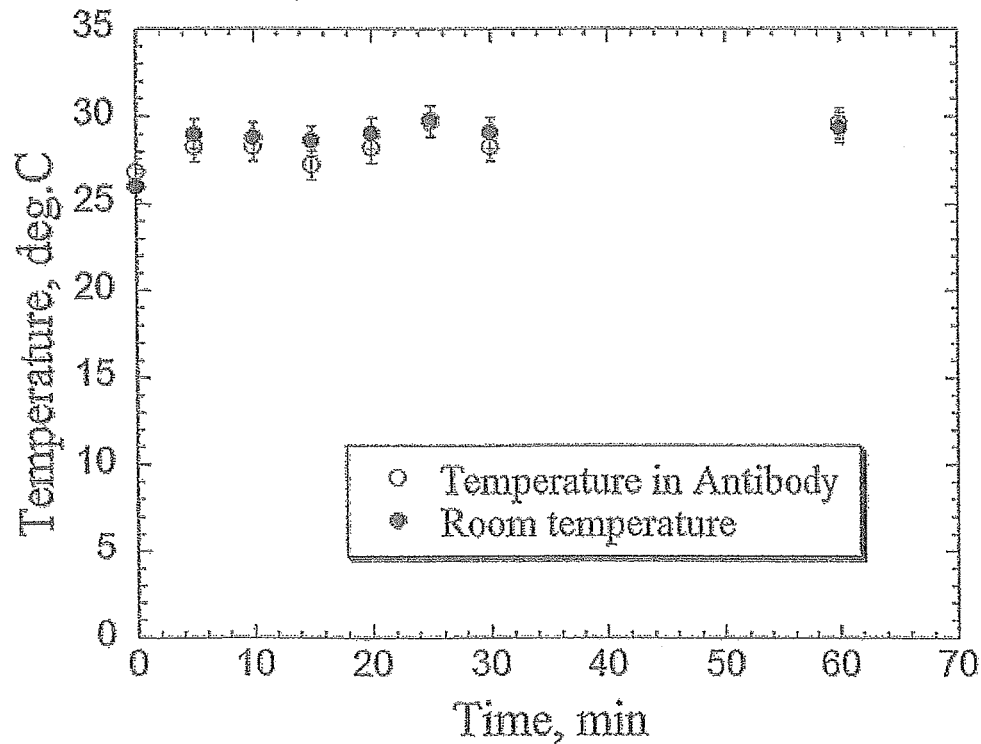
AT A FREQUENCY OF 91 Hz

F I G. 1 0
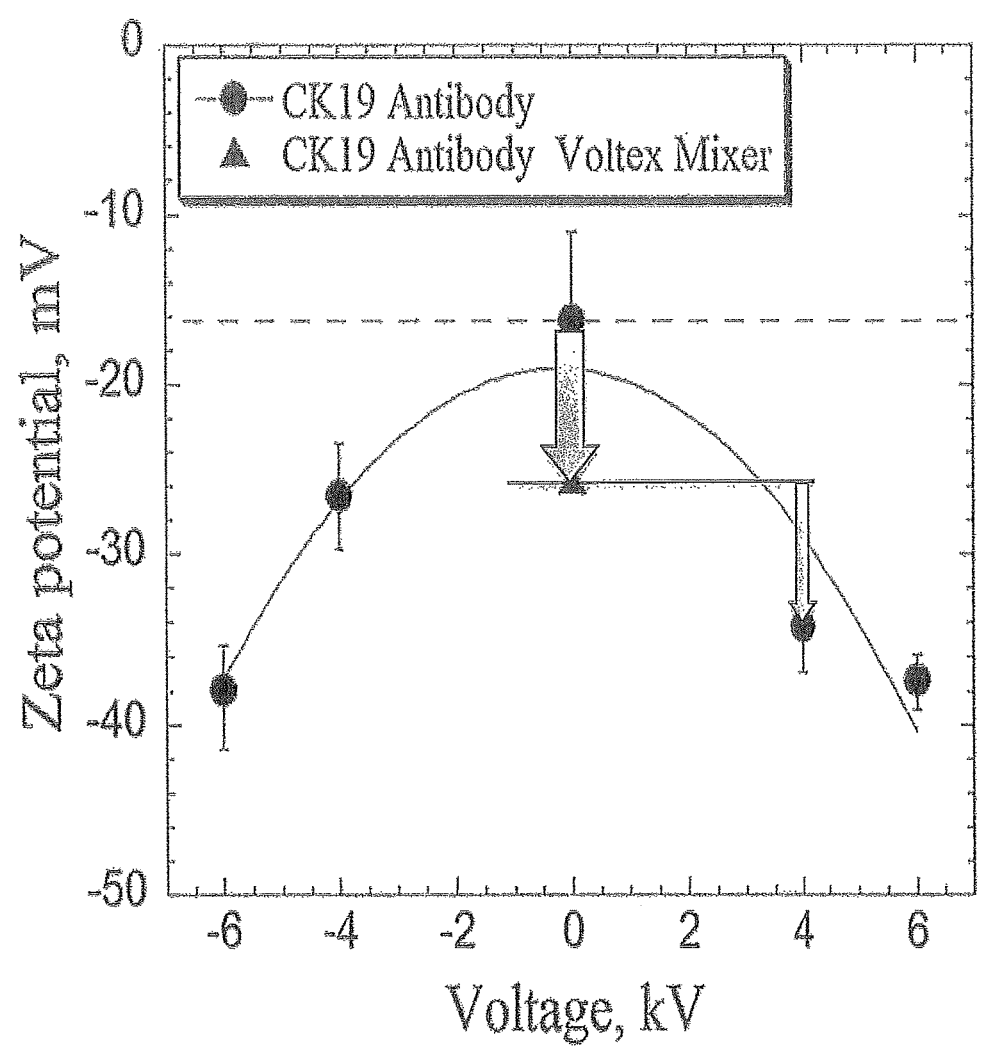

FIG.15
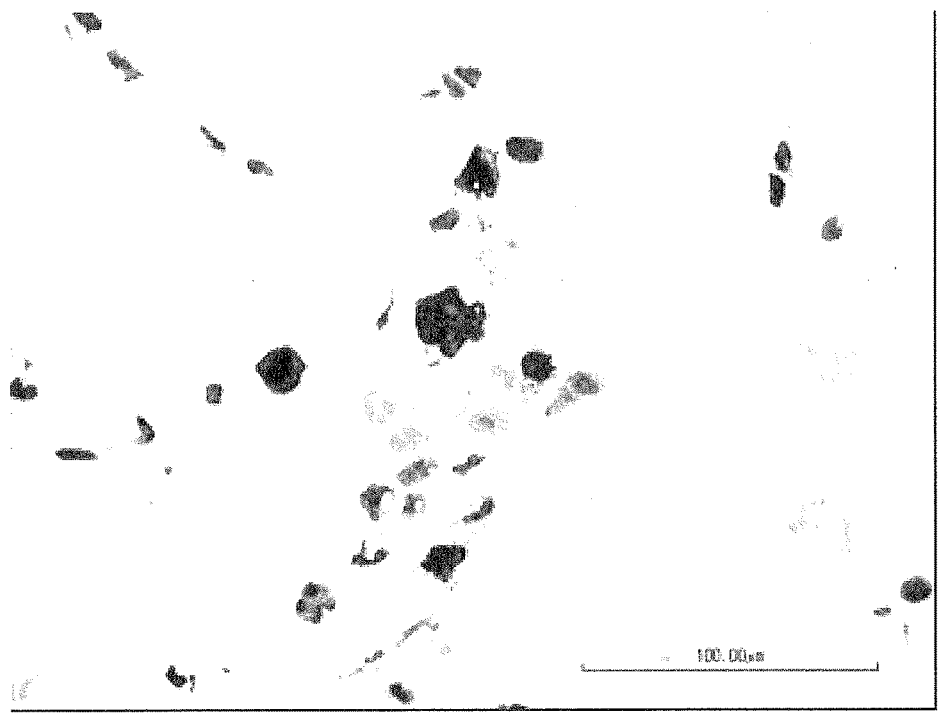
(a) COMPARATIVE EXAMPLE 4
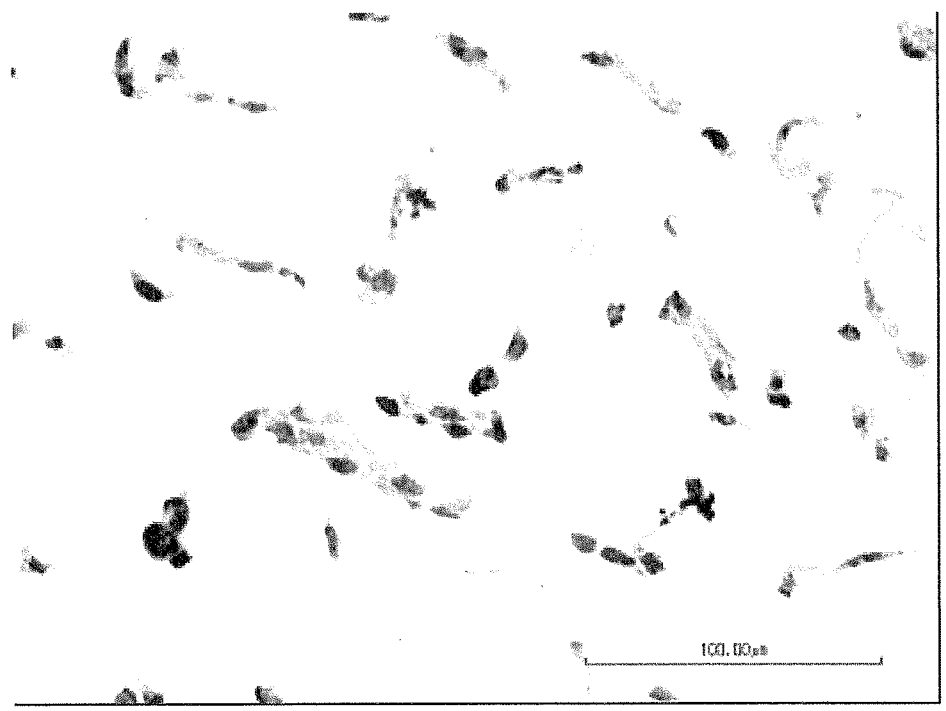
(b) EXAMPLE 1

FIG.16
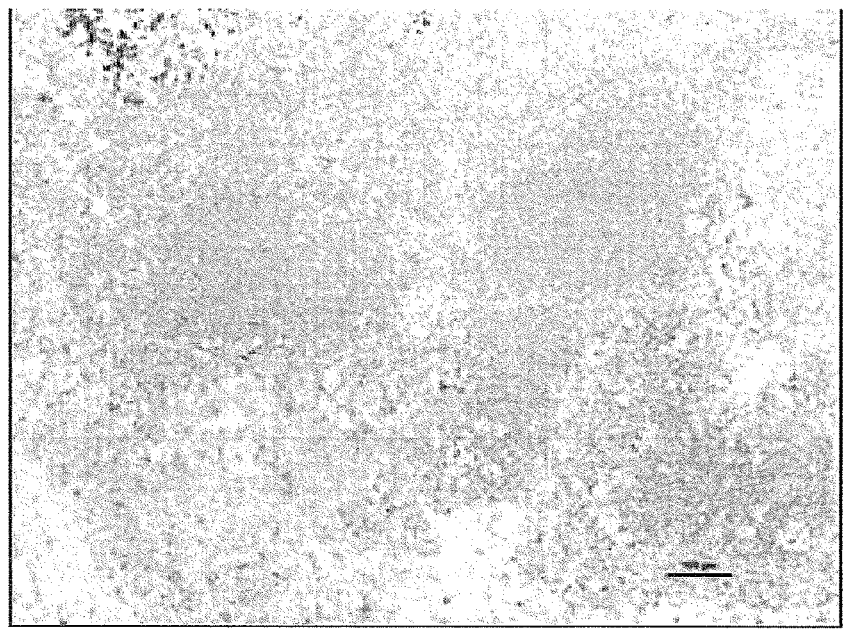
(a) COMPARATIVE EXAMPLE 5
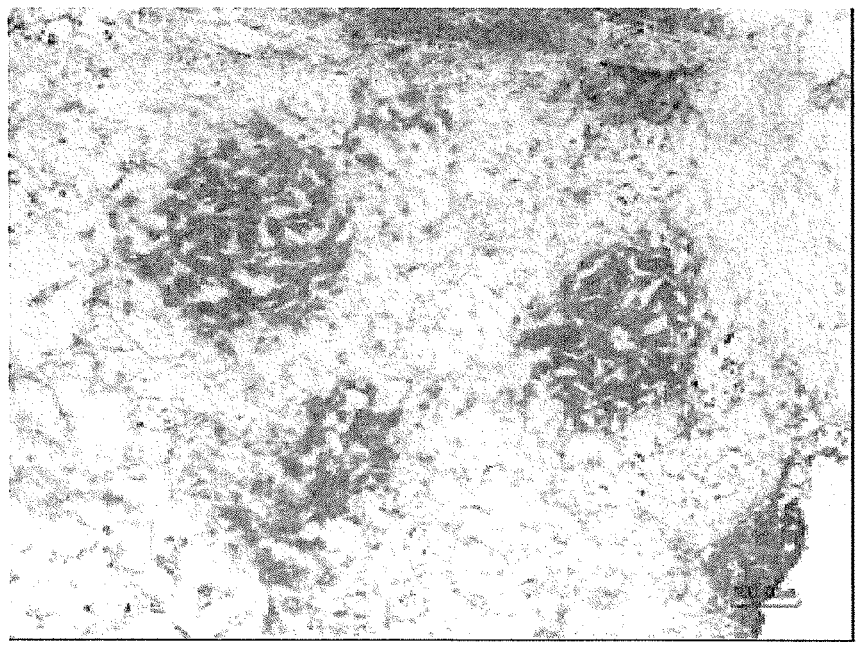
(b) EXAMPLE 2

APPARATUS FOR AUTOMATIC ELECTRIC FIELD IMMUNOHISTOCHEMICAL STAINING AND METHOD FOR AUTOMATIC ELECTRIC FIELD IMMUNOHISTOCHEMICAL STAINING

BACKGROUND OF THE INVENTION

Field of the Invention

The present invention relates to, for example, an automatic electric field immunohistochemical staining apparatus and an automatic electric field immunohistochemical staining method that can be used in intraoperative rapid pathological diagnosis of characterizing a subject tissue specimen (lesion site) within a limited length of time during surgical procedures or endoscopic surgery.

Description of the Prior Art

A physical phenomenon is known in which Coulomb force is generated by a high-voltage alternating electric field and this Coulomb force draws droplets in one direction. It is also known that droplets undergo vibration as the polarity of the applied high voltage is changed. Once droplets are drawn and vibrated, fine matter present in the droplets becomes stirred. The present inventors have focused on these physical phenomena and have, to date, developed a technology of contactlessly stirring minute droplets of not more than 1 mL, especially on the order of 50 to several hundred microliters, by applying a high-voltage alternating electric field. In particular, if this technology is applied to droplets containing antibodies, it is thought that the antibodies would be stirred in the droplets and become actively dispersed. The present inventors have proposed in Patent Reference 1 described below a non-contact stirring technique that significantly shortens the time required for, for example, an antigen fixation step, a blocking step, an antigen-antibody reaction step, and a color development reaction step in ELISA (hereinafter this technique may also be referred to as "electric field stirring technique").

PATENT REFERENCE

[Patent Reference 1] Japanese Unexamined Patent Application Publication No. 2010-119388

SUMMARY OF THE INVENTION

For intraoperative rapid pathological diagnosis for characterizing a lesion site in a limited length of time during surgical procedures or endoscopic surgery, HE staining (hematoxylin and eosin staining) that can perform staining in 5 minutes is presently used due to time constraints. However, since HE staining is a staining method for merely giving an overall picture of a cell or a tissue structure, it has a problem in that small residual tumors and lymph node micrometastasis are frequently overlooked. Meanwhile, in order to minimize the chance of overlooking residual tumors and lymph node metastasis, immunohistochemical staining that uses an antigen-antibody reaction identifiable by the presence or absence of a protein (antigen) serving as a pathogen can be effectively employed as intraoperative rapid pathological diagnosis. However, conventional immunohistochemical staining requires at least 2 hours to perform and thus has a problem in that it is not suitable for intraoperative rapid pathological diagnosis for which it is required to complete diagnosis within 40 minutes.

Note that although a lymph node metastasis diagnosis instrument that utilizes an OSNA method for performing gene amplification in about 30 minutes is commercially available, the metastasis diagnosis by this method lacks morphological information and thus is not reliable. Automatic immunohistochemical staining instruments are also commercially available but they have been developed for the purposes of performing immunohistochemical staining of a large quantity of samples at the same time and require at least 90 minutes to perform, which makes them unsuitable for intraoperative rapid pathological diagnosis.

Moreover, if intraoperative rapid pathological diagnosis by immunohistochemical staining is possible, it needs to be made widely available. In order to promote widespread adoption of this technique, it is desirable that preparation of samples for diagnosis be easy, the precision of the process steps be enhanced, all procedures be completed on commercially available glass slides, and ease of handling be increased, for example. In other words, automation of immunohistochemical staining that does not require manpower is required as well as acceleration of the immunohistochemical staining that does not require manpower. Accordingly, acceleration and automation of not only the reaction steps such as an antigen-antibody reaction of a primary antibody and an antigen and an antigen-antibody reaction of a secondary antibody and a primary antibody but also washing steps performed before and after the reaction steps are needed. Conventionally, the washing steps have been performed manually and thus manpower has been needed.

The present invention has been proposed in view of the above-described circumstances and an object thereof is to provide an automatic electric field immunohistochemical staining apparatus and an automatic electric field immunohistochemical staining method with which a high-voltage alternating electric field as proposed in Patent Reference 1 described above is applied to a subject to promote automation of a series of reactions constituting immunohistochemical staining through a technique of contactlessly stifling. In particular, the present invention aims to completely automate the steps of antigen-antibody reactions of antibodies and antigens and washing required before and after the antigen-antibody reactions while significantly reducing the time required to perform immunohistochemical staining and without increasing the temperature of samples during the reactions (stirring).

In order to achieve the objects described above, the present invention provides an automatic electric field immunohistochemical staining apparatus that accelerates and automates, by a stirring phenomenon based on electric field application, a series of reactions constituting immunohistochemical staining for detecting an antigen in a subject tissue specimen by using a predetermined antibody. The apparatus comprises a sample mounting unit having a stage on which a substrate with the tissue specimen fixed thereto is mounted; a solution supply unit provided with a container portion that contains a solution containing the antibody and a dripping member that drips the solution from the container portion onto the tissue specimen on the substrate; an electric field stirring unit provided with a first electrode having a plate shape or a ring shape; and a washing unit provided with a drain tube that drains the solution dripped onto the tissue specimen on the substrate.

In the automatic electric field immunohistochemical staining apparatus described above, preferably, the sample mounting unit can be transported back and forth or right and left.

The second electrode is disposed inside the sample mounting unit.

Preferably, the second electrode can be transported back and forth or right and left.

Preferably, the second electrode is disposed inside the stage.

Preferably, the container portion is provided in a cassette body.

Preferably, the first electrode has a penetrating hole.

Preferably, the drain tube can be moved in and out of the penetrating hole in the first electrode.

Preferably, when the sample mounting unit is transported and the substrate with the tissue specimen fixed thereto is positioned directly below the container portion of the solution supply unit, the solution is dripped onto the tissue specimen.

Preferably, when the sample mounting unit is transported and the substrate with the tissue specimen fixed thereto is positioned directly below the first electrode of the electric field stirring unit after dripping of the solution, an electric field is applied to the solution dripped onto the tissue specimen and the solution is stirred to perform the reaction.

Preferably, the solution is drained by using the drain tube of the washing unit from the tissue specimen on which the reaction has been performed.

Preferably, the washing unit is provided with a supply tube that supplies a washing solution for washing the tissue specimen to the tissue specimen on the substrate and the washing solution is supplied through the supply tube to the tissue specimen on which the reaction has been performed.

Preferably, the supply tube can be moved in and out of the penetrating hole in the first electrode.

Preferably, a plurality of divided regions are formed in the substrate and the tissue specimen can be mounted for each of these regions and a plurality of the first electrodes and the second electrodes are provided to correspond to the regions.

Preferably, a positive control or a negative control which serves as an indicator of whether or not an antigen-antibody reaction of the antigen and the antibody has been performed is fixed to the substrate.

In addition, protrusions are preferably formed in the first electrode symmetrically about the penetrating hole as a center point. Note that the automatic electric field immunohistochemical staining apparatus preferably has a function of activating the antigen by application of an electric field to the tissue specimen when the sample mounting unit is transported and the substrate with the tissue specimen fixed thereto is positioned directly below the first electrode of the electric field stirring unit.

Moreover, the present invention also provides an automatic electric field immunohistochemical staining method performed by using the automatic electric field immunohistochemical staining apparatus described above. The method is characterized by comprising a step of dripping a first solution containing a primary antibody that reacts with the antigen onto the tissue specimen and applying an electric field to the first solution to stir the first solution and to perform an antigen-antibody reaction of the antigen and the primary antibody.

In particular, the automatic electric field immunohistochemical staining method preferably comprises a step of aspirating and draining the first solution after the antigen-antibody reaction of the antigen and the primary antibody.

The automatic electric field immunohistochemical staining method preferably comprises a step of dripping a second solution containing a secondary antibody that reacts with the primary antibody onto the tissue specimen after aspirating and draining the first solution, and applying an electric field to the second solution to stir the second solution and to perform an antigen-antibody reaction of the primary antibody and the secondary antibody.

The automatic electric field immunohistochemical staining method preferably comprises a step of aspirating and draining the second solution after the antigen-antibody reaction of the primary antibody and the secondary antibody.

A process from performing the antigen-antibody reaction of the antigen and the primary antibody to aspirating and draining the second solution is preferably automated.

In the automatic electric field immunohistochemical staining method described above, the washing unit preferably includes a supply tube that supplies a washing solution for washing the tissue specimen to the tissue specimen on the substrate; after aspirating and draining the first solution and before performing the antigen-antibody reaction of the primary antibody and the secondary antibody, the washing solution is preferably supplied by the supply tube to the tissue specimen and the electric field is applied to the washing solution to stir the washing solution and wash the tissue specimen; and after aspirating and draining the second solution, the washing solution is preferably supplied by the supply tube to the tissue specimen and the electric field is applied to the washing solution to stir the washing solution and wash the tissue specimen.

Moreover, preferably, the first electrode has a penetrating hole and the supply tube can be moved in and out of the penetrating hole in the first electrode.

Preferably, a plurality of divided regions are formed in the substrate and the tissue specimen can be mounted for each of these regions, and a plurality of the first electrodes are provided to correspond to the regions.

A positive control or a negative control which serves as an indicator of whether or not an antigen-antibody reaction of the antigen and the antibody has been performed is preferably fixed to the substrate.

Note that the automatic electric field immunohistochemical staining method described above preferably comprises a step of mounting a substrate with the tissue specimen fixed thereto between the first electrode and the second electrode and applying an electric field to the tissue specimen to activate the antigen. In such a case, the process from activation of the antigen up to aspirating and draining the second solution can be automated in the present invention.

The present invention has a sample mounting unit on which a substrate with a tissue specimen fixed thereto is mounted, a solution supply unit that drips a solution containing an antibody onto the tissue specimen, and an electric field stirring unit that includes a second electrode that forms a pair with the first electrode and applies an electric field to the solution dripped onto the tissue specimen. Because of the coordinated operation of these units, a series of reactions constituting the immunohistochemical staining, such as dripping of a solution of an antibody or the like and performing an antigen-antibody reaction, can be automated. Moreover, a washing unit equipped with a drain tube for draining a solution of an antibody or the like dripped onto the tissue specimen is also included and draining of a solution of an antibody or the like can also be automated. In the present invention, due to these structures, acceleration and automation of a series of reactions constituting immunohistochemical staining have been successfully achieved. Accordingly, an automatic electric field immunohistochemical staining apparatus and an automatic electric field immunohistochemical staining method that can be applied to intraoperative rapid pathological diagnosis under severe time constraints can be provided.

In particular, when the electric field stirring unit includes a supply tube for supplying a washing solution for washing the tissue specimen and has a structure with which the washing solution is supplied from the supply tube to the tissue specimen, the washing process required before and after antigen-antibody reactions can also be accelerated and automated. Moreover, reliable immunohistochemical staining can be performed. Consequently, an automatic electric field immunohistochemical staining apparatus and an automatic electric field immunohistochemical staining method that can be reliably applied to intraoperative rapid pathological diagnosis under severe time constraints can be provided.

Furthermore, a plurality of tissue specimens can be simultaneously immunohistochemically stained by employing a structure in which a plurality of divided regions are formed in the substrate so that a tissue specimen can be mounted on each divided region and in which a plurality of the first electrodes and a plurality of the second electrodes are disposed to correspond to these regions. According to a structure in which a positive control or a negative control that serves as an indicator of whether an antigen-antibody reaction of an antigen and an antibody has been performed is fixed to a substrate, it becomes possible to guarantee validity and reliability of immunohistochemical staining of each lot. A structure in which a substrate with a tissue specimen fixed thereto is mounted between the first electrode and the second electrode and in which an antigen is activated by applying an electric field to the tissue specimen improves the ratio of the antigen immunohistochemically stained. Accordingly, the performance of the automatic electric field immunohistochemical staining apparatus and the automatic electric field immunohistochemical staining method of the present invention can be improved.

It should be noted that a structure in which protrusions are symmetrically formed in the first electrode about a penetrating hole as the center point causes imbalance in electric field distribution and thus the electric field can be applied in a concentrated manner onto local portions of the solution dripped onto the tissue specimen. As a result, the amount of the solution dripped can be decreased, the height of the droplet can be decreased, and the chances of the antibody coming into contact with the antigen in the tissue specimen can be increased. Moreover, the chances of the antibody coming into contact with the antigen in the tissue specimen can also be increased by decreasing the interelectrode distance between the first electrode and the second electrode, increasing the electric field strength, or the like.

BRIEF DESCRIPTION OF THE DRAWINGS

FIG. 9 Graphs showing that the temperature of a solution does not increase and stays substantially constant despite application of non-contact stirring technology employed in the automatic electric field immunohistochemical staining apparatus.

FIG. 10 An explanatory diagram showing an improvement in dispersibility of an antibody by using changes in zeta potential.

FIG. 15(a) a photomicrograph showing results of immunohistochemical staining obtained by a protocol of Comparative Example 4 and (b) a photomicrograph showing results of immunohistochemical staining obtained in Example 1.

FIG. 16(a) a photomicrograph showing results of immunohistochemical staining obtained in Example 2 and (b) a photomicrograph showing results of immunohistochemical staining obtained in Comparative Example 5.

DESCRIPTION OF THE PREFERRED EMBODIMENTS

In the description below, an embodiment of an automatic electric field immunohistochemical staining apparatus according to the present invention and an embodiment of an automatic electric field immunohistochemical staining method performed by using this apparatus are described in detail with reference to drawings. These embodiments are merely examples that embody the structure of the present invention. The present invention may be subject to various design changes as long as these changes do not deviate from the matters described in the Claims.

It should be noted that an automatic electric field immunohistochemical staining apparatus according to the present invention accelerates a series of reactions related to immunohistochemical staining for detecting antigens in subject tissue specimens by using predetermined antibodies owing to the stirring phenomenon caused by application of electric fields, and automates most of the series of reactions. Accordingly, the present invention makes it possible to apply immunohistochemical staining to an intraoperative rapid pathological diagnosis under time constraints. Moreover, since the automatic electric field immunohistochemical staining apparatus according to the present invention enables immunohistochemical staining with a diluted antibody reagent, in other words, economical use of reagents, the cost for immunohistochemical staining can be reduced. The present invention is not only applicable to intraoperative rapid diagnosis using frozen slices and immunohistochemical staining diagnosis using paraffin-embedded slices but also contributes acceleration and automation of hybridization of nucleic acids, other antigen-antibody reactions, etc.

Figure 1:
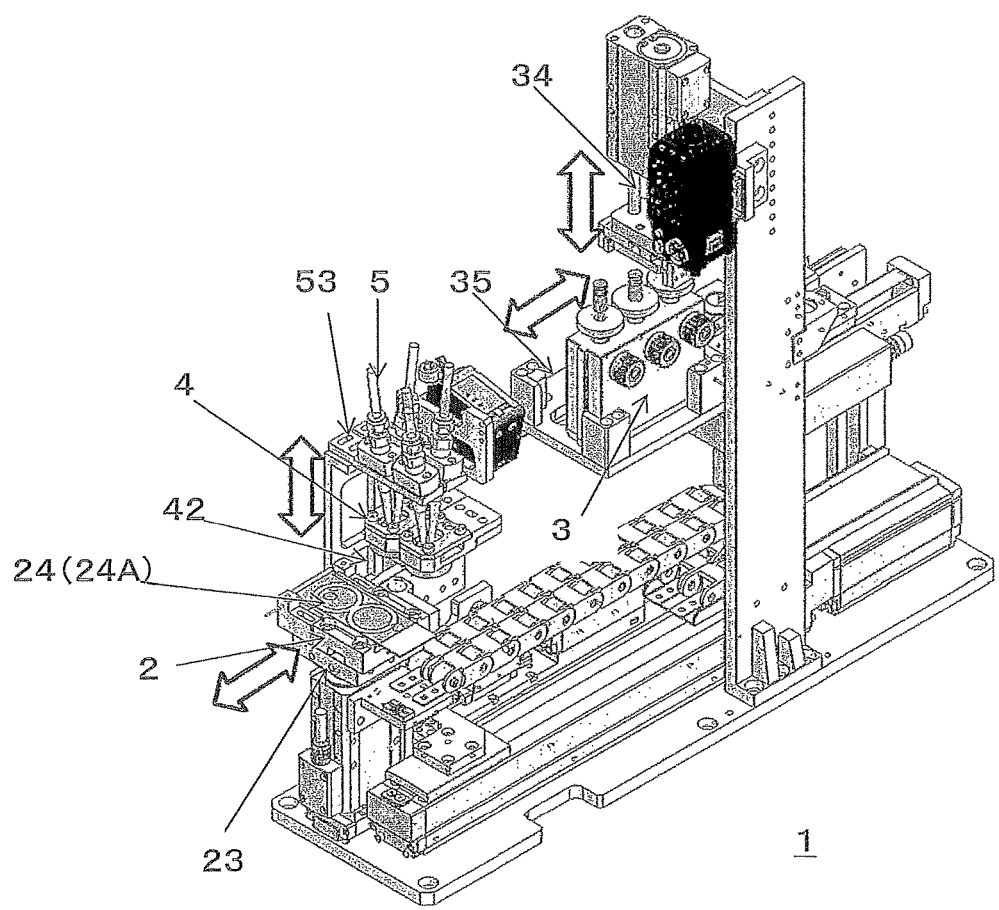
FIG. 1 A schematic perspective view schematically showing a whole automatic electric field immunohistochemical staining apparatus according to the present invention.

An automatic electric field immunohistochemical staining apparatus 1 according to the present invention has, as shown in FIG. 1, a sample mounting unit 2, a solution supply unit 3, an electric field stirring unit 4, and a washing unit 5 in its housing. Moreover, the housing is provide with a stage transport portion 23, a cassette transport portion 35, an upper electrode transport portion 42, and a washing tube transport portion 53 that respectively transport units (the sample mounting unit 2, the solution supply unit 3, the electric field stirring unit 4, and the washing unit 5). As the power sources of the respective transport portions, known power sources such as motors can be employed.

The automatic electric field immunohistochemical staining apparatus 1 can perform various functions as the sample mounting unit 2, the solution supply unit 3, the electric field stirring unit 4, and the washing unit 5 operates in coordination with one another. To be specific, the sample mounting unit 2 and the electric field stirring unit 4 operate so as to activate antigens in tissue specimens. The sample mounting unit 2 and the solution supply unit 3 operate so as to supply a solution or the like containing a predetermined antibody to a tissue specimen. The sample mounting unit 2 and the electric field stirring unit 4 operate so as to perform an antigen-antibody reaction for a tissue specimen to which the solution containing a predetermined antibody has been supplied. The sample mounting unit 2, the electric field stirring unit 4, and the washing unit 5 operate so as to, for example, drain a solution or the like containing a predetermined antibody and supply a washing solution so as to wash the tissue specimen. Note that, in the present invention, activating an antigen means that the reactivity of an antigen in a tissue specimen to an antibody is enhanced by application of an electric field to the tissue specimen before performing of the antigen-antibody reaction.

Figure 2:
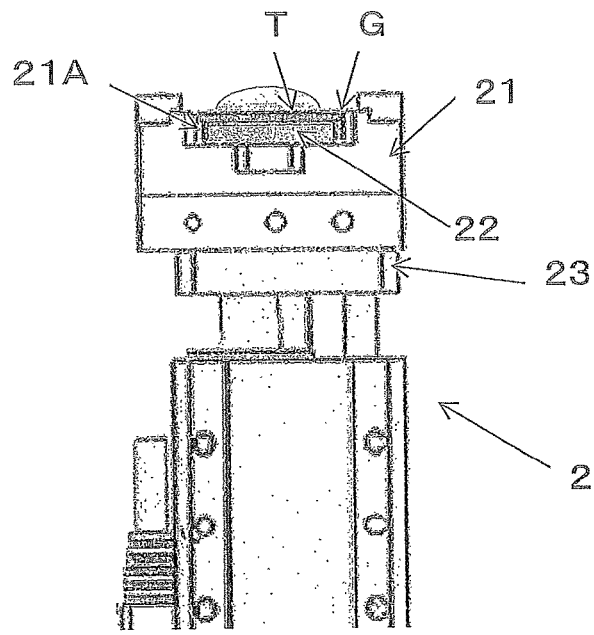
FIG. 2 A schematic side view of a sample mounting unit of the automatic electric field immunohistochemical staining apparatus.

As shown in FIGS. 1 and 2, the sample mounting unit 2 has a mounting portion 21A on which a glass substrate G, which is a substrate to which a tissue specimen T has been fixed, is mounted and a stage 21 capable of transporting the mounting portion 21A back and forth, right and left, or up and down. Inside the stage 21, a lower electrode 22, which is a second electrode, is disposed in proximity to the mounting portion 21A. The sample mounting unit 2 is configured to be attached to the stage transport portion 23 so that the stage 21 is transported back and forth or right and left. As the substrate to which the tissue specimen T is fixed, a glass substrate or a plastic substrate can be employed.

The stage 21 is transported by the stage transport portion 23 to each of the solution supply unit 3, the electric field stirring unit 4, and the washing unit 5. The stage 21 is recessed in the center portion and this recessed region serves as the mounting portion 21A. The glass substrate G is securely accommodated in the mounting portion 21A because the mounting portion 21A of the stage 21 is recessed. Moreover, the lower electrode 22 is disposed on the further inner side of the stage 21 than the mounting portion 21A and, in particular, is disposed directly below the mounting portion 21A. The lower electrode 22 may be formed of a known electrode material, such as highly conductive copper, an aluminum alloy, stainless steel, or indium tin oxide (ITO) which is a transparent electrode. The thickness of the lower electrode 22 is preferably 4 to 10 mm from the viewpoint of forming a stable electric field. The shape thereof may be a plate shape, a disk shape, a rod shape, or any other shape as long as an electric field can be formed with an upper electrode which is a first electrode described below.

Figure 12:
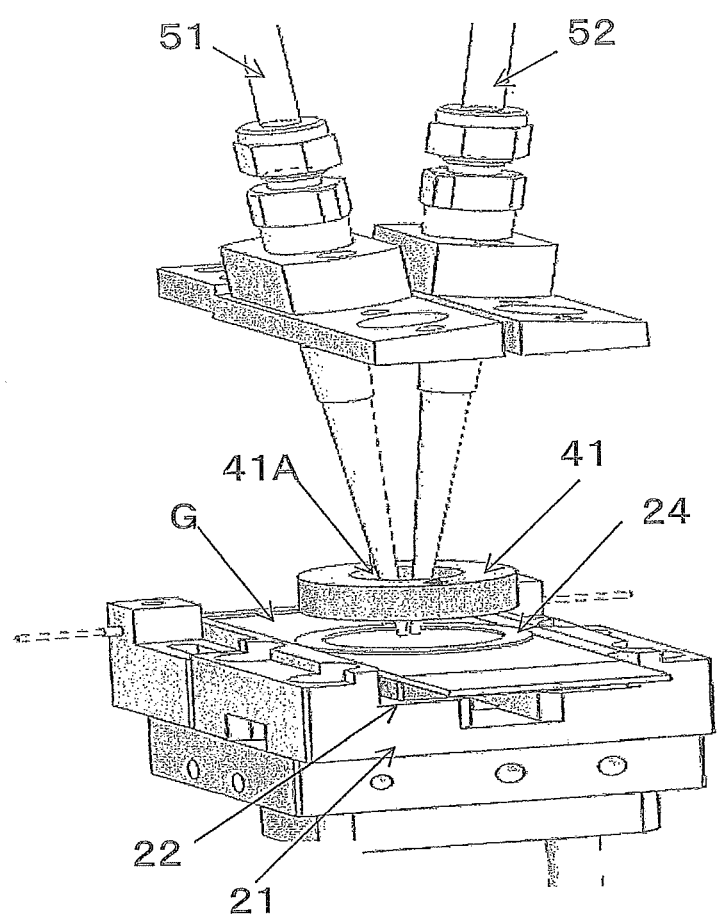
FIG. 12 An explanatory diagram showing the coordinated operation of the sample mounting unit, the electric field stirring unit and the washing unit of the automatic electric field immunohistochemical staining apparatus and how a tissue specimen is washed.

On the glass substrate G, a ring-shaped and water repellent water-repelling ring 24 that has a frame composed of a resin that is resistant to acetone and does not affect the electric field distribution is formed to surround the fixed tissue specimen T (also refer to FIG. 12). Because of the frame of the water-repelling ring 24, the solution dripped from the solution supply unit 3 forms a dome-shaped droplet on the tissue specimen T. The material of the water-repelling ring 24 is, for example, one selected from polyvinyl-based, polyvinyl chloride-based, silicone-based, or fluorine-based materials. Note that in FIG. 1, a two-hole-type water-repelling ring 24A formed of a frame in which two rings are formed is shown.

The solution dripped onto the water-repelling ring 24 forms a dome shape that forms a contact angle of 45 degrees or less on the tissue specimen T due to the frame which is a resin portion of the water-repelling ring 24. As a result, variation in the diameter of the bottom of the droplet is suppressed and the maximum height (peak position) becomes constant in accordance with the amount of solution dripped. Thus, the variation in distance between the peak position of the solution forming a dome shape and the electrode (lower electrode 22 or upper electrode 41) is suppressed, and as a result, variation in the extent of stirring during stirring of the solution by application of an electric field is suppressed. In other words, high-performance stirring with good reproducibility can be realized.

The automatic electric field immunohistochemical staining apparatus 1 does not require an adjusting mechanism for adjusting the distance between the peak position of the solution and the electrode for each lot, an adjusting mechanism for adjusting the electric field strength applied for each lot, and a mechanism for sensing the height of the dripped solution and the structure thereof can be simplified.

The present invention is not limited to the water-repelling ring 24 described above and some type of a water-repelling frame may be disposed on the glass substrate G so as to surround the fixed tissue specimen T. Furthermore, it is also possible to draw a circle or a rectangle on the glass substrate G by using an ink having a water-repelling function. A water-repelling treatment agent may be applied so as to surround the tissue specimen T fixed onto the glass substrate G so as to form a water-repelling portion on the glass substrate G.

The glass substrate G can be, for example, a glass slide having a width of 26 mm, a length of 76 mm, and a thickness of 0.8 mm. The water-repelling ring 24 has an inner diameter of 10 mm to 20 mm and the width of the resin portion forming the frame is 0.5 mm to 3 mm and preferably 2 mm to 3 mm in order to allow the solution to form a dome shape having a contact angle of 45 degrees or less. The thickness of the water-repelling ring 24 is preferably 0.15 mm to 0.3 mm. Alternatively, for example, a rectangular water-repelling frame can be employed and the amount of solution dripped may be within the range of 3000 μL or less. However, the amount of solution dripped is preferably 8 to 1000 μL from the standpoint of uniformity of stirring.

Figure 3:
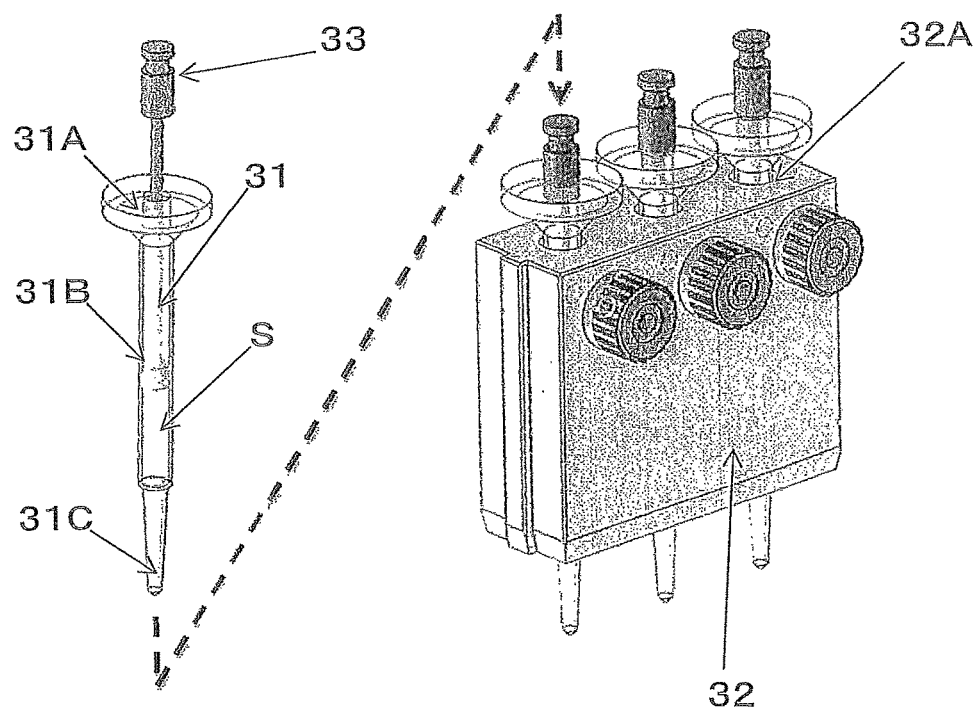
FIG. 3 A schematic perspective view showing a relevant part of a solution supply unit of the automatic electric field immunohistochemical staining apparatus and an explanatory diagram of a cylinder and a plunger rod of the solution supply unit.

As shown in FIGS. 1 and 3, the solution supply unit 3 includes a cassette body 32 that includes a cylinder 31 serving as a container portion that contains, for example, a solution S containing a primary antibody as the antibody that reacts with the antigen in the tissue specimen T. Also, a plunger rod 33 that can be moved in and out of the cylinder 31 and that serves as a dripping member for dripping the primary-antibody-containing solution S or the like from the cylinder 31 toward the tissue specimen T on the glass substrate G is provided. The solution supply unit 3 is provided with a piston 34 that presses the plunger rod 33 during dripping of the solution S containing a primary antibody or the like. The cassette body 32 is attached to the cassette transport portion 35 that transports the cassette body 32 back and forth, right and left, or up and down.

The cylinder 31 is a tubular body constituted by a flange portion 31A having a wide opening that facilitates feeding of the primary-antibody-containing solution S or the like, a main body portion 31B that contains the solution S or the like, and a tip portion 31C that serves as a guiding path for performing dripping toward the tissue specimen T on the glass substrate G. The cassette body 32 is formed with penetrating holes that penetrate in the vertical direction formed therethrough. The penetrating holes have a shape corresponding to the cylinder 31 and serve as a cylinder housing portion 32A for housing the cylinders 31. The plunger rod 33 drips the solution S or the like onto the glass substrate G upon being pressed with the piston 34.

In this embodiment, the respective cylinders 31 contain, for example, a secondary antibody solution containing a secondary antibody that reacts with the primary antibody, a blocking solution for endogenous peroxidase removal required for immunohistochemical staining, and other reagents, in addition to the solution S containing a primary antibody that reacts with the antigen in the tissue specimen T. Moreover, in the solution supply unit 3, which plunger rod 33 of which cylinder 31 is to be pressed with the piston 34 is determined at the time of transporting the cassette body 32 by the cassette transport portion 35. In other words, which type of solution is to be dripped onto the tissue specimen T on the glass substrate G is determined at the time of transporting the cassette body 32 by the cassette transport portion 35.

Figure 4:
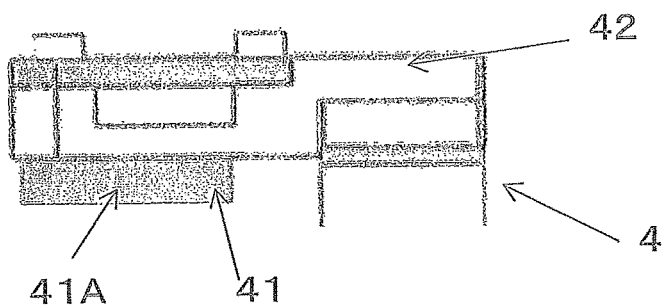
FIG. 4 A schematic side view of an electric field stirring unit of the automatic electric field immunohistochemical staining apparatus.

As shown in FIGS. 1 and 4, the electric field stirring unit 4 is provided with the upper electrode 41, which is the first electrode that has an annular shape with a penetrating hole 41A (also refer to FIG. 12) and forms a pair with the lower electrode 22 of the sample mounting unit 2, in this embodiment. Moreover, the electric field stirring unit 4 is attached to the upper electrode transport portion 42 and transported back and forth, right and left, or up and down. As with the lower electrode 22, the upper electrode 41 can also use a known electrode material, such as highly conductive copper, aluminum alloys, stainless steel, and indium tin oxide (ITO) which is a transparent electrode. The thickness thereof is preferably 4 to 10 mm from the viewpoint of forming stable electric fields. The shape thereof may be a plate shape as long as a penetrating hole is formed.

Figure 5:
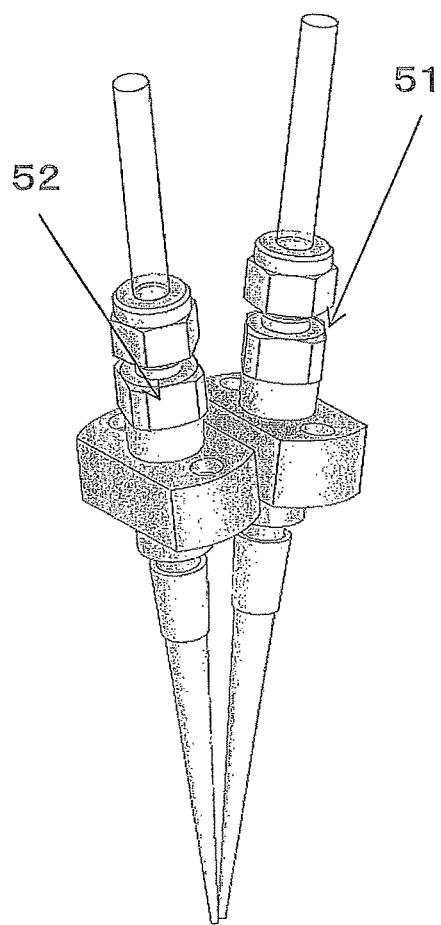
FIG. 5 A schematic perspective view showing a relevant part of a washing unit of the automatic electric field immunohistochemical staining apparatus.

As shown in FIGS. 1 and 5, the washing unit 5 is provided with a drain tube 51 that drains the primary-antibody-containing solution S or the like dripped toward the tissue specimen T on the glass substrate G and a supply tube 52 for supplying a washing solution for washing the tissue specimen T toward the tissue specimen T on the glass substrate G. The drain tube 51 and the supply tube 52 are attached to the washing tube transport portion 53. The washing tube transport portion 53 transports the drain tube 51 and the supply tube 52 back and forth, right and left, or up and down so that these tubes can be moved in and out of the penetrating hole 41A of the upper electrode 41. Furthermore, although not shown in the drawing, a drain-tube-connecting tube for discharging the solution S or the like to outside from the drain tube 51 is connected to the drain tube 51 and a supply-tube-connecting tube for supplying a washing solution to the supply tube 52 from outside is connected to the supply tube 52.

Note that, as the washing fluid, PBS (phosphate buffered saline) can be named as an example for use in immunohistochemical staining. The present invention is not limited to PBS and various types of washing solution that can effectively perform immunohistochemical staining can be employed. PBS blended with NaCl, KCl, NaHPO$_4$, or KH$_2$PO$_4$ may be used. A washing solution having a composition that contains calcium or magnesium can be employed. Alternatively, a washing solution containing a surfactant may be used.

Figure 6:
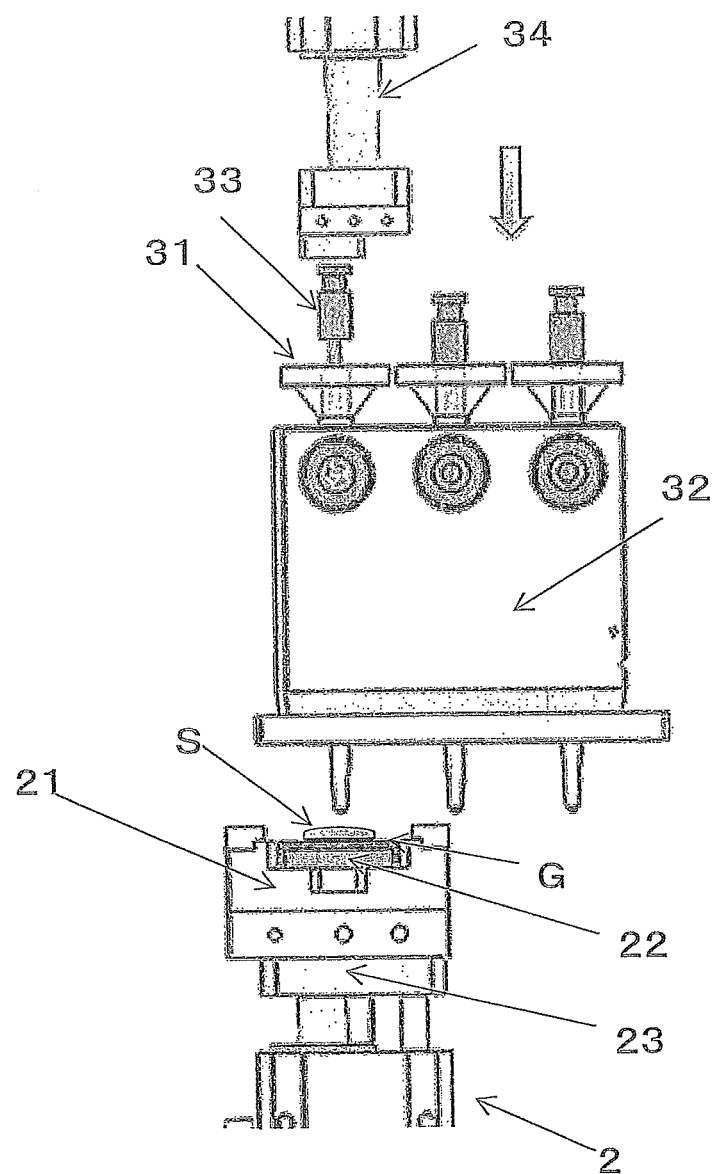
FIG. 6 An explanatory diagram illustrating the coordinated operation of the sample mounting unit and the solution supply unit of the automatic electric field immunohistochemical staining apparatus and how a solution is supplied to a tissue specimen.

In the automatic electric field immunohistochemical staining apparatus 1 according to the present invention, as shown in FIG. 6, when the sample mounting unit 2 is transported and the glass substrate G with the tissue specimen T fixed thereto is positioned directly below a predetermined cylinder 31 of the solution supply unit 3, the solution contained in the cylinder 31 is dripped onto the tissue specimen T. For example, a solution S containing a primary antibody is dripped onto the tissue specimen T.

First, which solution (a solution S containing a primary antibody, a secondary antibody solution containing a secondary antibody that reacts with the primary antibody, a blocking solution for removing endogenous peroxidase, or other reagent) is to be dripped onto the tissue specimen T on the glass substrate G is determined. Then the cassette body 32 is transported by the cassette transport portion 35 so that the piston 34 is positioned directly above the plunger rod 33 of the cylinder 31 that contains the determined solution (in FIG. 6, the solution S containing a primary antibody). At the same time, the stage 21 onto which the glass substrate G with the tissue specimen T fixed thereto is mounted is transported by the stage transport portion 23 up to a position directly below the cylinder 31 containing the solution S containing a primary antibody, which is the determined solution.

Next, the plunger rod 33 of the cylinder 31 containing the solution S containing a primary antibody is pressed with the piston 34. Consequently, the solution S containing a primary antibody is dripped through the tip portion 31C of the cylinder 31 onto the glass substrate G with the tissue specimen T fixed thereto. The amount of the solution S dripped containing a primary antibody pressed with the piston 34 and dripped is 5 to 600 μL at a time.

Note that there may be cases where one of the secondary antibody solution, blocking solution, or other reagent described above is dripped onto the glass substrate G with the tissue specimen T fixed thereto, in addition to the solution S containing a primary antibody. In such cases also, a similar coordinated operation of the sample mounting unit 2 and the solution supply unit 3 described above causes the selected solution to be dripped onto the glass substrate G with the tissue specimen T fixed thereto. The amount of the secondary antibody solution dripped may be 5 to 600 μL at a time. The amount of the blocking solution to be dripped for removing the endogenous peroxidase is preferably 5 to 1000 μL at a time.

Figure 7:
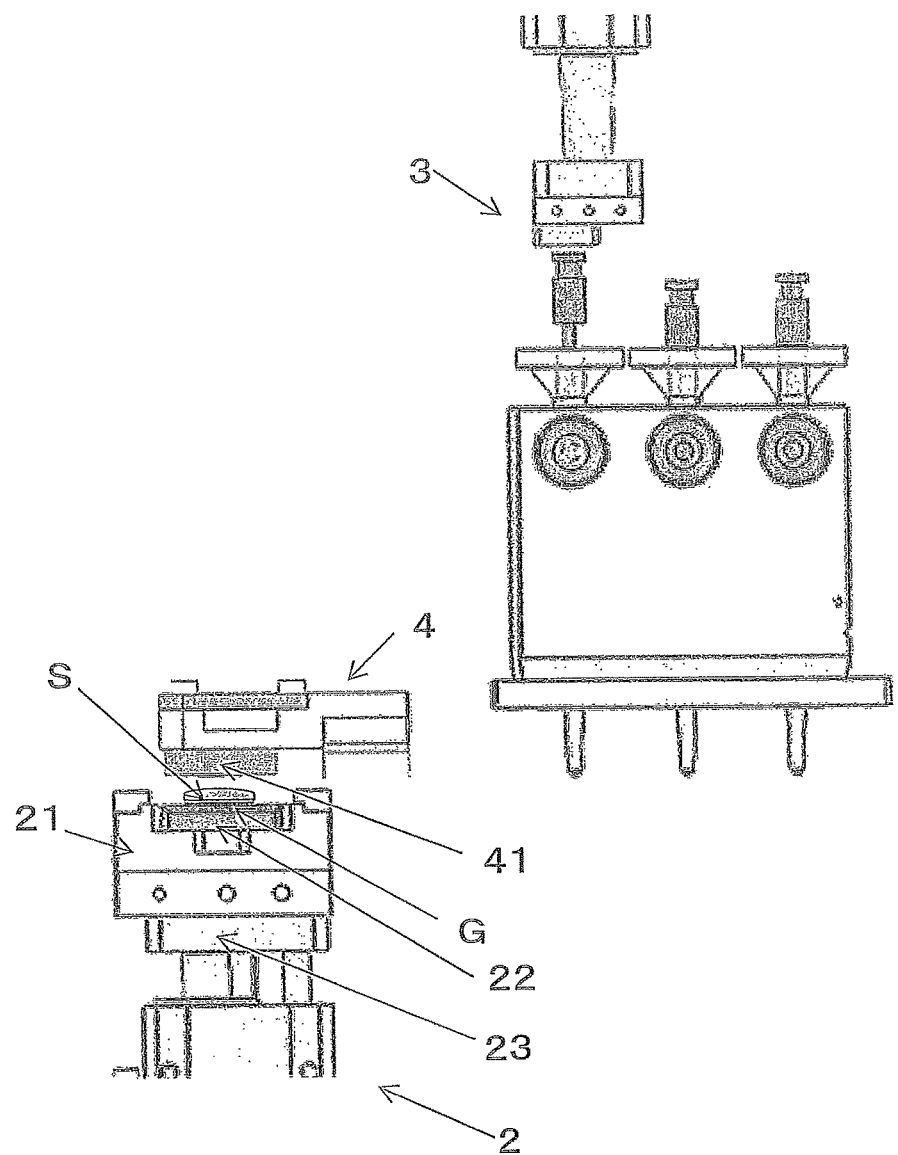
FIG. 7 An explanatory diagram illustrating the coordinate operation of the sample mounting unit and the electric field stirring unit of the automatic electric field immunohistochemical staining apparatus and how a solution is stirred.

In the present invention, as shown in FIG. 7, the sample mounting unit 2 and the electric field stirring unit 4 operate in coordination so as to perform an antigen-antibody reaction on the tissue specimen T to which the primary-antibody-containing solution S or the like is supplied. Moreover, the antigen in the tissue specimen T is activated.

First, the stage 21 on which the glass substrate G with the tissue specimen T to which the solution (in FIG. 7, solution S containing a primary antibody) is dripped is mounted is transported by the stage transport portion 23 up to a position directly below the upper electrode 41 of the electric field stirring unit 4. Then an electric field is applied to the tissue specimen T and between the upper electrode 41 and the lower electrode 22 of the sample mounting unit 2 and stirring of the solution S containing a primary antibody causes an antigen-antibody reaction of the primary antibody in the primary-antibody-containing solution S and the antigen in the tissue specimen T to proceed.

To be specific, in an environment with humidity controlled to 60±20%, as the main voltage of an applied electric field strength, a repeated square-wave alternating electric field with a plus-side bias generated by adding an offset electric field strength of 0.15 to 0.7 kV/mm to 0.4 to 1.5 kV/mm on the plus side is applied. In particular, as the applied alternating electric field, a frequency at which the solution S containing a primary antibody is actively stirred is selected from the range of 0.1 to 300 Hz. Such an alternating electric field is formed between the upper electrode 41 and the lower electrode 22 and the solution S containing a primary antibody is stirred. Note that either of the upper electrode 41 and the lower electrode 22 may be set to the plus side. When the applied electric field strength is stronger than 1.5 kV/mm on the plus side, there is a possibility of discharge and when it is less than 0.4 kV/mm, there is a possibility that stirring would not occur. At an offset voltage stronger than 1 kV/mm, there is a possibility of discharge, and when it is less than 0.2 kV/mm, there is a possibility that discharge would not occur. In the present invention, the antigen-antibody reaction of the primary antibody and the antigen in the tissue specimen T is performed in a 2significantly shorter time than in the conventional art and takes 5 to 7 minutes.

When an electric field is formed between the upper electrode 41 and the lower electrode 22, the solution dripped onto the glass substrate G may be, in addition to the solution S containing a primary antibody, a secondary antibody solution, a blocking solution, or other reagent in some cases. In such cases also, the solution is stirred by the coordinated operation of the sample mounting unit 2 and the electric field stirring unit 4. Accordingly, a series of reactions constituting immunohistochemical staining, such as an antigen-antibody reaction of a primary antibody and a secondary antibody and a reaction of suppressing non-specific reactions, can be accelerated by stirring based on application of an electric field.

Here, the mechanism in the automatic electric field immunohistochemical staining apparatus 1 for accelerating the antigen-antibody reaction etc., by stirring based on application of an electric field is described with reference to FIG. 8.

Figure 8:
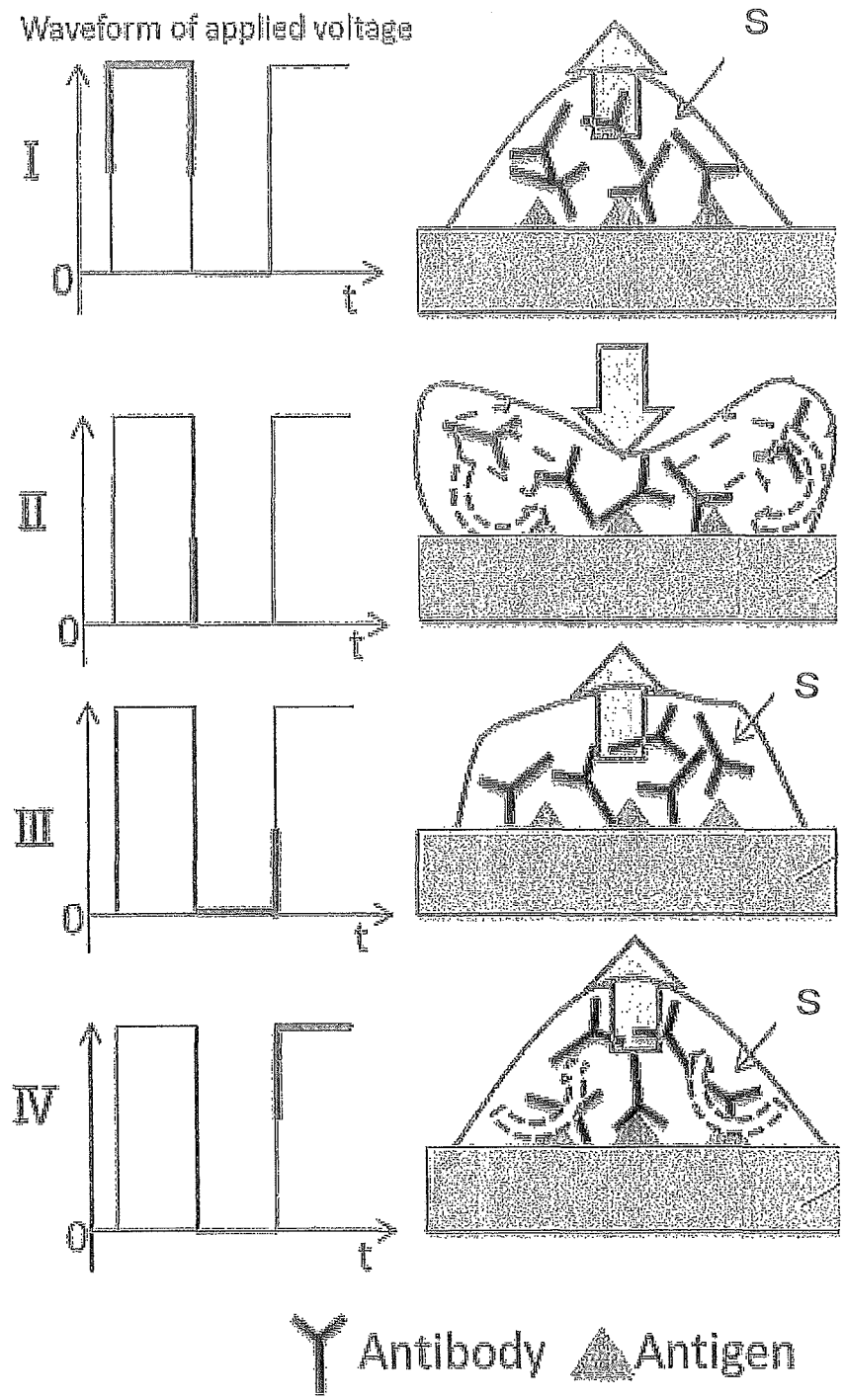
FIG. 8 Schematic explanatory diagrams that illustrate non-contact stirring technology employed in the automatic electric field immunohistochemical staining apparatus.

As shown in FIG. 8, at the moment the alternating electric field formed between the upper electrode 41 and the lower electrode 22 exhibits a protruding waveform, the solution to be stirred (for example, the solution S containing a primary antibody) is drawn toward the upper electrode 41 (refer to I in FIG. 8). Moreover, at the moment the alternating electric field exhibits a recessed (dented) waveform, the solution to be stirred is drawn toward the lower electrode 22 and exhibits a dented shape (refer to II in FIG. 8). Furthermore, the solution to be stirred recovers from the dented shape at the moment the waveform thereof returns to a protruding shape (refer to III in FIG. 8), and subsequently, is drawn toward the upper electrode 41 again as the waveform exhibits a protruding shape (refer to IV in FIG. 8). Because of such stirring, particles (primary antibody and the like) undergoing Brownian motion in the solution have their motion speed accelerated and their chances of coming into contact with the antigen are increased. As a result, the antigen-antibody reaction is accelerated.

The temperature of the solution under stirring rarely increases, as shown in FIG. 9, since the selected frequency is a low frequency in the range of 0.1 to 300 Hz. FIG. 9 shows the results of investigating the increase in the temperature of the solution when the amount of solution is 150 μL, the interelectrode distance between the upper electrode 41 and the lower electrode 22 is 5.4 mm, the applied voltage is 3 kV, and the frequency is 21 Hz and 91 Hz. Thus, as long as the automatic electric field immunohistochemical staining apparatus 1 is used at room temperature, non-specific reactions attributable to denaturation of proteins and tissues rarely occur. Moreover, FIG. 10 shows that application of an electric field at a predetermined application strength to the solution by using the automatic electric field immunohistochemical staining apparatus 1 causes stirring to progress and improves dispersibility, which is demonstrated by the shift in zeta potential in the minus direction by stirring. Note that the point marked by a solid triangle (▲) in FIG. 10 indicates the value of the zeta potential observed when a desired solution was stirred with a known desktop voltex mixer.

Figure 11:
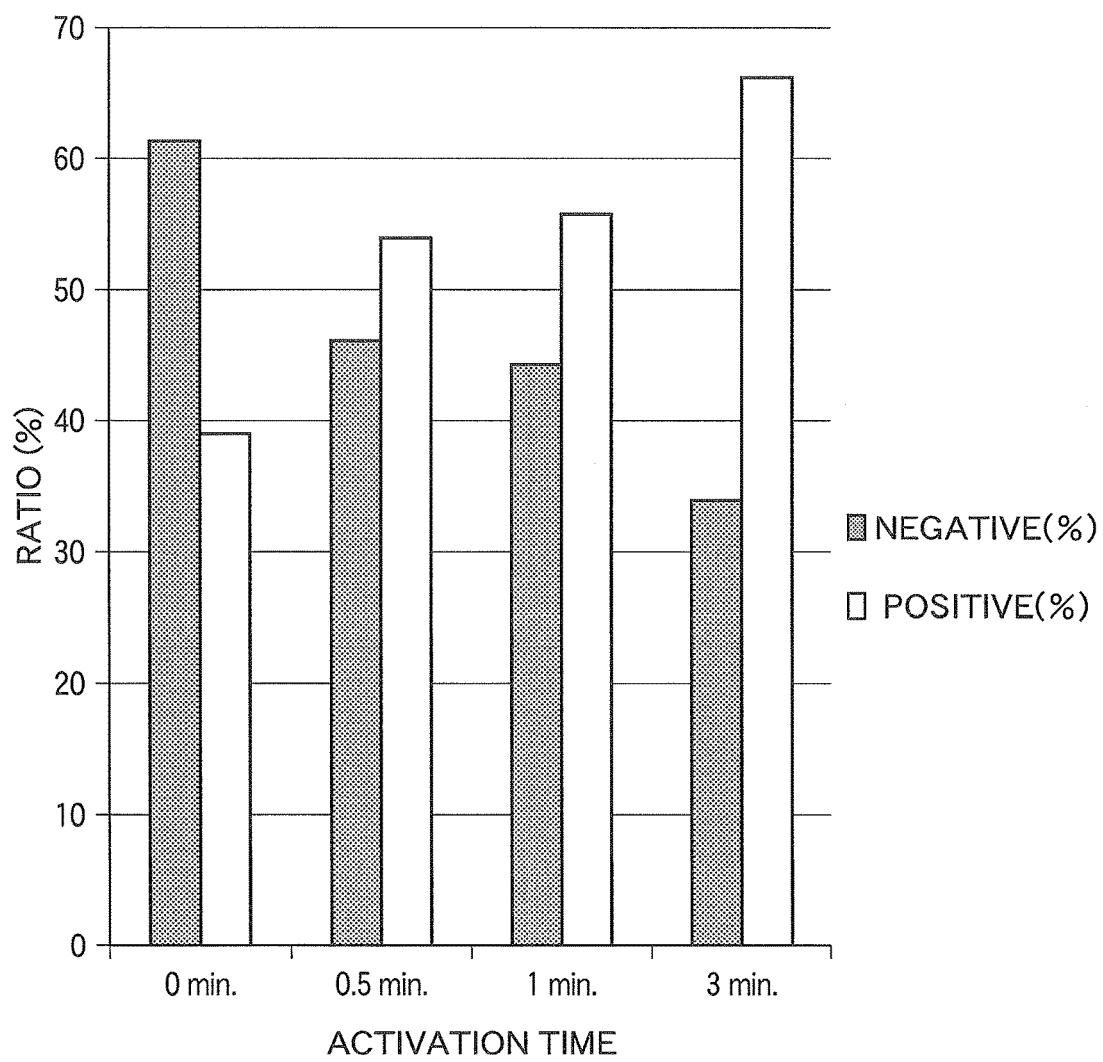
FIG. 11 An explanatory diagram showing that application of an electric field to a tissue specimen prior to an antigen-antibody reaction of an antigen and a primary antibody in an automatic electric field immunohistochemical staining apparatus improves the ratio of successful immunohistochemical staining compared to the cases in which no electric fields are applied.

In the present invention, although not shown in the drawings, the sample mounting unit 2 and the electric field stirring unit 4 operate in coordination so that when the glass substrate G to which the tissue specimen T is fixed is positioned directly below the upper electrode 41 of the electric field stirring unit 4, an electric field is applied to the tissue specimen T and the antigen in the tissue specimen T is activated. Note that activation of the antigen is performed prior to supplying the primary-antibody-containing solution S or the like to the tissue specimen T fixed to the glass substrate G. As shown in FIG. 11, before the antigen-antibody reaction of the antigen and the primary antibody, an electric field is applied to the tissue specimen T and this improves the ratio of successful immunohistochemical staining compared to when no electric field is applied and thus the reactivity of the antigen is increased. In FIG. 11, samples in which the antigen is activated by applying an electric field for 30 seconds to 3 minutes show an increase in ratio of successful immunohistochemical staining by about 10% to 30% compared to samples to which no electric field is applied.

In order to activate the antigen by using the automatic electric field immunohistochemical staining apparatus 1, first, the stage 21 on which the glass substrate G with the tissue specimen T fixed thereon is mounted is transported by the stage transport portion 23 up to a position directly below the upper electrode 41 of the electric field stirring unit 4. Then an electric field is applied to the tissue specimen T and between the upper electrode 41 and the lower electrode 22 of the sample mounting unit 2 so as to activate the antigen in the tissue specimen T.

To be specific, as the main voltage of an applied electric field strength, a repeated square-wave alternating electric field with a plus-side bias generated by adding an offset electric field strength of 0.25 to 1 kV/mm to 0.4 to 2 kV/mm on the plus side is applied. In particular, as the applied alternating electric field, an appropriate frequency at which the antigen actively responses is selected from the range of 0.1 to 20 Hz. Such an alternating electric field is formed between the upper electrode 41 and the lower electrode 22. The length of time for activating the antigen is preferably 30 seconds to 3 minutes.

In the automatic electric field immunohistochemical staining apparatus 1, when the antigen is activated, the environment is controlled to a humidity of 60±20%. Moreover, either of the upper electrode 41 and the lower electrode 22 may be set to the plus side.

In the present invention, as shown in FIG. 12, the sample mounting unit 2, the electric field stirring unit 4, and the washing unit 5 operate in coordination so that the tissue specimen T is washed as, for example, the solution (the primary-antibody-containing solution S in FIG. 12) on the glass substrate G is drained and a washing solution is supplied to the glass substrate G. Note that during this washing, the stage 21 on which the glass substrate G with the tissue specimen T fixed thereto is mounted is maintained at the position directly below the upper electrode 41.

First, on the tissue specimen T in which the antigen-antibody reaction of the antigen and the primary antibody has been performed, while the tip of the drain tube 51 is moved in and out of the penetrating hole 41A of the upper electrode 41, the primary-antibody-containing solution S dripped onto the tissue specimen T on the glass substrate G is aspirated and drained. Consequently, the antigen in the tissue specimen T and the unreacted primary antibody are removed from the glass substrate G.

Furthermore, toward the tissue specimen T from which the primary-antibody-containing solution S has been drained by the drain tube 51, while the tip of the supply tube 52 is moved in and out of the penetrating hole 41A of the upper electrode 41, a washing solution is supplied toward the tissue specimen T on the glass substrate G. In particular, after the washing solution is fed to the tissue specimen T on the glass substrate G through the supply tube 52, an electric field is applied to the washing solution on the glass substrate G and the tissue specimen T is washed by stirring of the washing solution.

To be specific, as the main voltage of an applied electric field strength, a repeated square-wave alternating electric field with a plus-side bias generated by adding an offset electric field strength of 0.15 to 0.7 kV/mm to 0.4 to 1.5 kV/mm on the plus side is applied. In particular, as the applied alternating electric field, an appropriate frequency at which the washing solution is actively stirred is selected from the range of 0.1 to 300 Hz. Such an alternating electric field is formed between the upper electrode 41 and the lower electrode 22 and stirs the washing solution. When the applied electric field strength is stronger than 1.5 kV/mm on the plus side, there is a possibility of discharge and when it is less than 0.4 kV/mm, there is a possibility that stirring would not occur. Furthermore, at an offset voltage stronger than 1 kV/mm, there is a possibility of discharge, and when it is less than 0.2 kV/mm, there is a possibility that discharge would not occur. The amount of the washing solution supplied each time of washing is preferably 5 to 1000 µL. In applying the alternating electric field to the washing solution also, either of the upper electrode 41 and the lower electrode 22 may be set to the plus side.

The washing solution after washing of the tissue specimen T is aspirated and drained through the drain tube 51 and the antigen in the tissue specimen T and the unreacted primary antibody are thereby removed from the glass substrate G. Consequently, not only the washing time can be shortened compared to conventional manual washing but also staining variation can be suppressed because of stable washing.

Note that the solution dripped onto the glass substrate G may be, in addition to the primary-antibody-containing solution S, a secondary antibody solution, a blocking solution, or other reagent. In such a case also, a similar coordinated operation of the sample mounting unit 2 and the washing unit 5 described above removes these solutions and supply a washing solution and the tissue specimen T on the glass substrate G can be appropriately washed.

Moreover, draining of the solution by using the drain tube 51 and supplying of the washing solution by using the supply tube 52 can be achieved by driving a device such as a known pump. Such washing of the tissue specimen T can be repeated plural times. Repeating the draining of the solution by using the drain tube 51 and supplying of the washing solution by using the supply tube 52 plural times can ensure suppression of staining variation. The numbers and arrangements of drain tubes 51 and the supply tubes 52 are not particularly limited; however, as described above, an example thereof is a structure in which one tube is provided for each or in which one supply tube 52 is disposed at the center and one or more drain tubes 51 are disposed around the supply tube 52, for example.

According to the present invention, the process including activation of an antigen, an antigen-antibody reaction of the antigen and a primary antibody, PBS washing, removal of an endogenous peroxidase, PBS washing, an antigen-antibody reaction of the primary antibody and a secondary antibody, and PBS washing can be automated.

Figure 13A:
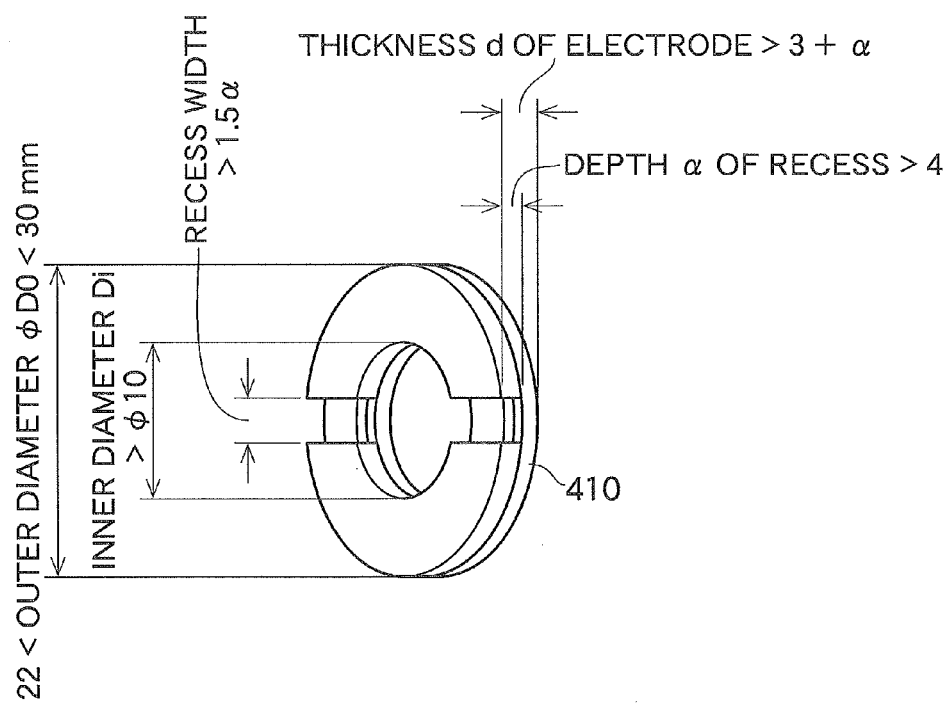
FIG. 13(a) an enlarged view showing an electric field concentration-type electrode which is another example of an upper electrode of an electric field stirring unit and (b) an explanatory diagram schematically illustrating the flow of a droplet by use of arrows when the electric field concentration-type electrode is used.
Figure 13B:
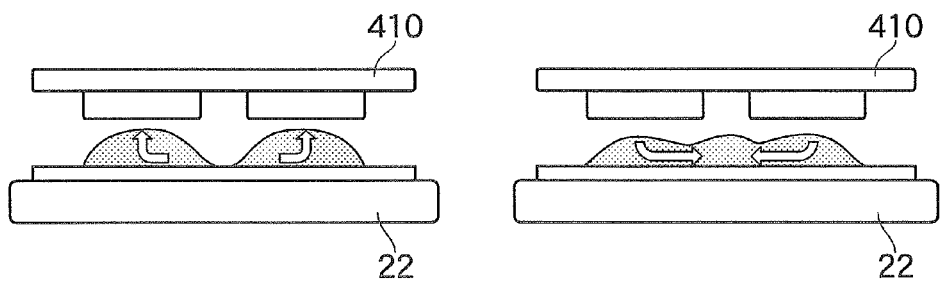

Here, in constructing an automatic electric field immunohistochemical staining apparatus according to the present invention, an electric field concentration-type upper electrode 410, which has two protrusions symmetrically arranged about the penetrating hole as the center point so that the electric field is locally concentrated as shown in FIG. 13(a), may be employed as the first electrode of the electric field stirring unit. As shown in FIG. 13(b), due to the shape of the protrusions, distribution of the electric field formed between the upper electrode and the lower electrode becomes imbalanced and the solution surface is drawn at portions whose number corresponds to the number (two) of protrusions formed; thus, a higher stirring effect can be obtained. Moreover, during stirring, because the resin portion of the water-repelling ring 24 functions as a breakwater to cause the solution to bounce back inward, turbulence flow is generated in the solution and the stirring can be further activated.

Moreover, since the surface of the solution is drawn at portions whose number corresponds to the number (two) of protrusions formed, the height of the solution drawn is decreased and the frequency of particles (primary antibody and the like) in the solution coming into contact with the tissue specimen can be increased. Moreover, since the height of the solution drawn is decreased, the interelectrode distance can be further decreased, the electric field strength can be increased, and the stirring effect can also be enhanced. Because the stirring effect is intensified, the length of time required to perform the antigen-antibody reaction can also be shortened.

The protrusions are preferably formed in 2 or more and 6 or less places symmetrically about the penetrating hole as the center point. The penetrating hole preferably has an inner diameter of less than 10 mm and the outer diameter of the electric field concentration-type upper electrode is preferably 22 mm to 30 mm. In addition, the thickness of the electric field concentration-type upper electrode is preferably 3 mm+α mm assuming that the depth of the recess (dent) between the protrusions is α mm. Moreover, the width between the protrusions is preferably 1.5α mm assuming that the depth of the recess (dent) between the protrusions is α mm.

With the electric field concentration-type upper electrode 410, a higher stirring effect is obtained; thus, it is advantageous in performing stirring for an antigen-antibody reaction and stirring during washing. However, in activating an antigen, it is preferable to apply an electric field by using the upper electrode 41 described above.

Figure 14:
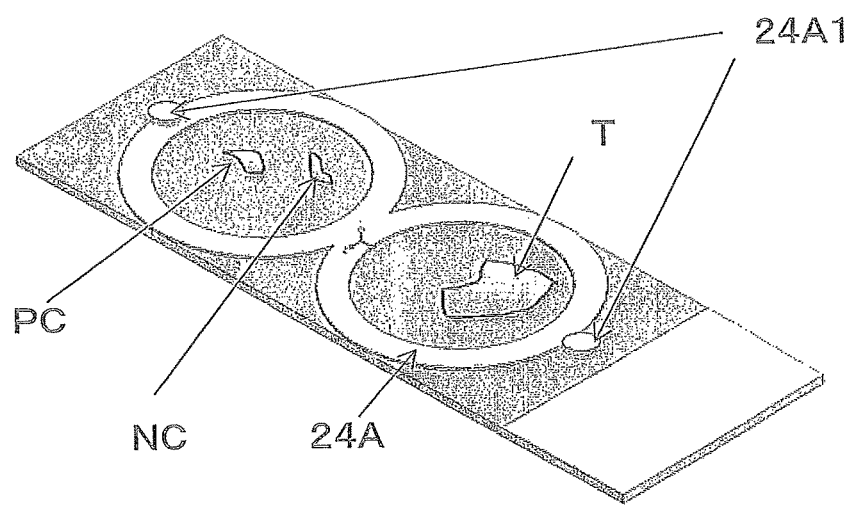
FIG. 14 is an explanatory diagram illustrating a two-hole-type water-repelling ring formed on a substrate to be mounted on the sample mounting unit.

Moreover, in constructing an automatic electric field immunohistochemical staining apparatus according to the present invention, plural divided regions can be formed in the substrate and tissue specimens can be respectively mounted on these regions so that plural tissue specimens can be immunohistochemically stained at the same time. To be specific, for a water-repelling ring disposed on the substrate, a two-hole-type water-repelling ring 24A having a frame with two rings having an inner diameter of 20 mm may be employed so that two divided dripping regions are formed as shown in FIG. 14. To comply with this, the automatic electric field immunohistochemical staining apparatus 1, as shown in FIG. 1, has two upper electrodes 41 and two lower electrodes 22 based on plural regions formed by the water-repelling ring 24A. Moreover, two supply tubes 52 and two drain tubes 51 are also provided.

Moreover, as shown in FIG. 14, a positive control PC or a negative control NC that allows visual recognition of whether or not the solution (for example, the primary-antibody-containing solution S) has been stirred can be fixed to the inner side of the water-repelling ring 24A on the glass substrate G. The positive control PC develops a color once stirred and the negative control NC becomes uncolored once stirred. Accordingly, coloring of the positive control PC or un-coloring of the negative control NC can be used as an indicator of whether or not the immunohistochemical staining reaction has been performed.

For example, as shown in FIG. 14, a positive control PC or a negative control NC is fixed inside one of the rings of the water-repelling ring 24A having two rings on the glass substrate G and a tissue specimen T is fixed inside the other ring. By using the glass substrate of such a type, a series of reactions constituting immunohistochemical staining is conducted by using an automatic electric field immunohistochemical staining apparatus according to the present invention. Then whether or not the series of reactions is conducted appropriately can be determined by using the positive control PC or negative control NC as an indicator, staining failure can be avoided, and performance of immunohistochemical staining can be improved.

Tags 24A1 that allow easy separation from the glass substrate G are preferably provided at one or two positions on the frame which is the resin portion of the water-repelling ring 24A. Moreover, the water-repelling ring can have a three-ring frame formed therein if the inner diameter is about 10 mm (not shown in the drawing).

Alternatively, the automatic electric field immunohistochemical staining apparatus according to the present invention may be provided with a heating mechanism. The lower electrodes is heated with, for example, a heater such as a Peltier element. This is because heating the lower electrode from 35 to 38° C. improves the reactivity of the antigen-antibody reaction.

EXAMPLES

An example of a basic protocol in accordance with an automatic electric field immunohistochemical staining method that uses an automatic electric field immunohistochemical staining apparatus according to the present invention is shown in [Table 1] below. Moreover, [Table 2] below shows comparative examples which are examples of conventional protocols related to immunohistochemical staining using kits commercially available from various companies.

TABLE 1

| Staining steps | In the apparatus | Present invention (Example 1 and Example 2) |
|---|---|---|
| 1. Acetone fixation | Hand method | 2 minutes |
| 2. PBS washing | Hand method | 15 seconds |
| 3. Electric field activation | Mounted into the apparatus | 30 seconds to 60 seconds |
| 4. Primary antibody | Mounted into the apparatus | 5 to 7 minutes |
| 5. Electric field PBS washing | Mounted into the apparatus | 30 seconds to 60 seconds |
| 6. Endogenous peroxidase removal | Mounted into the apparatus | 1 minute |
| 7. Electric field PBS washing | Mounted into the apparatus | 30 seconds to 60 seconds |
| 8. Secondary antibody | Mounted into the apparatus | 5 minutes |
| 9. Electric field PBS washing | Removed from the apparatus | 1 minute |
| 10. DAB color development | Hand method | 2 minutes |
| 11. Washing, nuclear staining, and sealing | Hand method | 1 minute |
| | | 22.5 minutes or shorter |

TABLE 2

| Staining steps | Comparative Example 1 | Comparative Example 2 | Comparative Example 3 | Comparative Example 4 |
|---|---|---|---|---|
| PBS washing | — | 10 minutes × 3 | — | — |
| Acetone fixation | 4° C., 10 minutes | As needed | 10 minutes | 4° C., 10 minutes |
| PBS washing | 5 minutes × 2 | 10 minutes × 3 | As needed | 5 minutes × 3 |
| Endogenous peroxide removal | 10 minutes | 10 minutes | 5 to 10 minutes | — |

TABLE 2-continued

| Staining steps | Comparative Example 1 | Comparative Example 2 | Comparative Example 3 | Comparative Example 4 |
|---|---|---|---|---|
| PBS washing | 5 minutes × 2 | 5 minutes × 3 | 5 minutes × 3 | — |
| Blocking | 60 minutes | 60 minutes | 20 minutes | — |
| PBS washing | — | — | 5 minutes × 3 | — |
| Primary antibody | 4° C., overnight (480 minutes or longer) | 60 minutes | Room temperature, 60 minutes | 60 minutes |
| PBS washing | 5 minutes × 3 | 5 minutes × 3 | 5 minutes × 3 | 5 minutes × 3 |
| Secondary antibody | Room temperature, 30 minutes | 60 minutes | 45 minutes | 30 minutes |
| PBS washing | 5 minutes × 3 | 5 minutes × 3 | 5 minutes × 3 | 5 minutes × 3 |
| Avidin-biotin conjugate solution | Room temperature, 30 minutes | 30 minutes | 15 minutes | — |
| PBS washing | 5 minutes × 3 | 5 minutes × 3 | 30 seconds | — |
| DAB color development | As needed | As needed | 5 minutes | 5 minutes |
| Washing, nucleus staining, and stealing | 12 minutes | As needed | 3 minutes | 1 minute |
| Total time | 697 minutes or longer | 340 minutes or longer | 223 minutes or longer | 151 minutes |

That is, as shown in [Table 1], according to an automatic electric field immunohistochemical staining method of the present invention, a tissue specimen is fixed to a glass substrate with acetone and washed with PBS, and the glass substrate with the tissue specimen fixed thereto is mounted on a mounting portion of a sample mounting unit of an automatic electric field immunohistochemical staining apparatus. In such a state, the automatic electric field immunohistochemical staining apparatus is operated.

In the automatic electric field immunohistochemical staining apparatus, the sample mounting unit is transported; the glass substrate with the tissue specimen fixed thereto is positioned directly below an upper electrode of an electric field stirring unit; and an electric field is applied for 30 to 60 seconds to the tissue specimen so as to activate the antigen in the tissue sample. Subsequently, the sample mounting unit is transported; the glass substrate to which the tissue specimen containing the activated antigen is fixed is positioned directly below a container portion of a solution supply unit, the container portion containing a primary-antibody-containing solution; and the primary-antibody-containing solution is dripped onto the tissue specimen. Furthermore, the sample mounting unit is transported; the glass substrate is positioned directly below the upper electrode of the electric field stirring unit; an electric field is applied for 5 to 7 minutes to the tissue specimen onto which the primary-antibody-containing solution has been dripped, and an antigen-antibody reaction of the primary antibody and the antigen in the tissue specimen is performed by non-contact stirring of the primary-antibody-containing solution.

After the antigen-antibody reaction of the antigen and the primary antibody, a washing unit is transported, the tip of a drain tube is delivered to the primary-antibody-containing solution through the penetrating hole in the upper electrode, and the solution containing the primary antibody is aspirated and drained. Moreover, the tip of a supply tube of the washing unit peers through the penetrating hole in the upper electrode toward the tissue specimen and PBS serving as a washing solution is supplied to the glass substrate. An electric field is applied to the PBS for 30 to 60 seconds and the tissue specimen is washed with PBS by non-contact stirring. The PBS used for washing is aspirated and drained through the drain tube from the glass substrate.

Next, in the automatic electric field immunohistochemical staining apparatus, the sample mounting unit is transported; the glass substrate to which the tissue specimen washed with PBS after completion of the antigen-antibody reaction of the antigen and the primary antibody is fixed is positioned directly below a container unit of the solution supply unit, the container unit containing a blocking solution for removing an endogenous peroxidase; and the blocking solution is dripped. The sample mounting unit is transported, the glass substrate to which the tissue specimen onto which the blocking solution has been dripped is fixed is positioned directly below the upper electrode of the electric field stirring unit, and an electric field is applied to the tissue specimen for 1 minute. Non-contact stirring of the blocking solution effectively suppress non-specific coloring for a chromogenic agent (diaminobenzidine solution or DAB solution) used in immunohistochemical staining.

After stirring of the blocking solution, the washing unit is transported, the tip of the drain tube is delivered to the blocking solution through the penetrating hole in the upper electrode, and the blocking solution is aspirated and drained. Moreover, the tip of the supply tube of the washing unit is directed toward the tissue specimen through the penetrating hole in the upper electrode, and PBS is supplied to the glass substrate. An electric field is applied to the PBS for 30 to 60 seconds and the tissue specimen is washed with PBS by non-contact stirring. The PBS used for washing is aspirated and drained by the drain tube from the glass substrate.

Furthermore, in the automatic electric field immunohistochemical staining apparatus, the sample mounting unit is transported; the glass substrate to which the tissue specimen that underwent the antigen-antibody reaction of the antigen and the primary antibody, washing with PBS, and blocking with the blocking solution is fixed is positioned directly below a container portion of the solution supply unit, the container portion containing a secondary antibody solution; and the secondary antibody solution is dripped. Then the sample mounting unit is transported, the glass substrate to which a tissue specimen onto which the secondary antibody solution has been dripped is fixed is positioned directly below the upper electrode of the electric field stirring unit, and an electric field is applied to the tissue specimen for 5 minutes. Non-contact stirring of the secondary antibody solution causes the antigen-antibody reaction of the primary antibody and the secondary antibody to proceed.

After the antigen-antibody reaction of the primary antibody and the secondary antibody, the washing unit is transported, the tip of the drain tube is delivered to the secondary antibody solution through the penetrating hole in the upper electrode, and the secondary antibody solution is aspirated and drained. Moreover, the tip of the supply tube of the washing unit is directed toward the tissue specimen through the penetrating hole in the upper electrode and supplies PBS serving as a washing solution onto the glass substrate. An electric field is applied to the PBS for 1 minute and the tissue specimen is washed with PBS by non-contact stirring. Furthermore, the PBS used for washing is aspirated and drained through the drain tube from the glass substrate. Then the operation of the automatic electric field immunohistochemical staining apparatus is stopped and the glass substrate that underwent a series of reactions is removed from the sample mounting unit to outside.

Subsequently, the tissue specimen on the glass substrate is subjected to the same treatments as those of conventional immunohistochemical staining, such as coloring with diaminobenzidine (DAB color development) that reacts with a peroxidase which is a marker enzyme of the secondary antibody, staining of a cell nucleus by nuclear staining, and sealing for anti-fading.

According to the automatic electric field immunohistochemical staining method of the present invention, the automatic electric field immunohistochemical staining apparatus is used and thus the operation of from acetone fixation to DAB color development, nuclear staining, sealing, etc., which are a series of reactions constituting the immunohistochemical staining, can be completed in about 22.5 minutes. Moreover, because the automatic electric field immunohistochemical staining apparatus is used, the process from activation of the antigen to washing after the antigen-antibody reaction using the secondary antibody can be automated.

In contrast, as shown in [Table 2], conventional immunohistochemical staining methods (Comparative Examples 1 to 3) that use commercially available kits from various companies require at least 223 minutes to perform the operation of from acetone fixation, to DAB color development, nuclear staining, sealing, etc.

Furthermore, Comparative Example 4 is an example of immunohistochemical staining with which, while the antigen-antibody reaction of the primary antibody and the antigen in the tissue specimen and the antigen-antibody reaction of the primary antibody and the secondary antibody are performed by an electric field stirring technique that uses an electric field stirring technique disclosed in Japanese Unexamined Patent Application Publication No. 2010-119388 which is Patent Reference 1 described above, the washing steps performed before and after these reactions are performed manually. In the case of Comparative Example 4, the operation from acetone fixation to DAB color development, nuclear staining, sealing, etc., required 151 minutes to perform.

In particular, the time required for the antigen-antibody reaction of the primary antibody and the antigen and the antigen-antibody reaction of the primary antibody and the secondary antibody is about 60 minutes or longer in Comparative Examples 1 to 4. In contrast, in the present invention, each reaction is shortened to 5 minutes. Moreover, in washing steps before and after the antigen-antibody reactions, performance of 3 sets of washing, 5 minutes each, i.e., 15 minutes or longer, is required in comparative examples. In contrast, in the present invention, this is shortened to 30 to 60 seconds or 1 minute.

Example 1

In Example 1, immunohistochemical staining was performed on a positive control by using an automatic electric field immunohistochemical staining apparatus of the present invention. The basic protocol was as described in [Table 1] above. A photomicrograph of results of immunohistochemical staining of Example 1 is shown in FIG. 15(b). FIG. 15(a) shows a photomicrograph of results of immunohistochemical staining obtained by the protocol of Comparative Example 4.

Furthermore, the primary antibody and the secondary antibody used in immunohistochemical staining and the amounts thereof, the amount of washing solution, and the inner diameter of the water-repelling ring in Example 1 are shown in [Table 3] below.

TABLE 3

| Tissue | | Positive control |
|---|---|---|
| Antibody | | Anti-Ki-67 Antibody (mib-1) |
| | Primary antibody | IR series diluted antibodies for tissue staining produced by DAKO |
| | Secondary antibody | Envision produced by DAKO |
| Amount | Antibody | 200 μL |
| | Washing solution | 400 μL |
| Diameter of water-repelling ring | | 20 mm |

In Example 1, the electric field conditions applied in activating the antigen in the positive control specimen were as follows. A square-wave electric field was applied to a tissue specimen on a glass substrate for 1 minute at an application electric field strength of 4.5 kV and a frequency of 1 Hz. The gap between the electrode and the tissue specimen was 3.3 mm.

Furthermore the electric field conditions applied in performing the antigen-antibody reaction of the primary antibody and the antigen were as follows. Into a water-repelling ring having an inner diameter of 20 mm and toward the tissue specimen on the glass substrate, 200 μL of a solution containing a primary antibody was dripped and a square-wave electric field was applied for 4 minutes and 30 seconds to this solution under conditions of applied electric field strength: 4 kV, offset voltage: 2 kV, and frequency: 1 to 30 Hz. The gap between the electrode and the solution was 4.5 mm.

The electric field conditions applied in performing the washing step after the antigen-antibody reaction of the primary antibody and the antigen were as follows. After the solution containing the primary antibody was drained by using the drain tube, 400 μL of PBS serving as a washing solution was supplied to the tissue specimen on the glass substrate by using the supply tube 12 and a square-wave electric field was applied for 30 seconds to the washing solution under conditions of applied electric field strength: 4 kV, offset voltage: 2 kV, and frequency: 1 to 30 Hz. The gap between the electrode and the washing solution was 6 mm. Subsequently, the washing solution was drained by using the drain tube. Note that in the washing step, the washing time was 30 seconds and the number of times of the washing was 1, which was sufficient.

The electric field conditions applied in performing the antigen-antibody reaction of the primary antibody and the secondary antibody were as follows. Into a water-repelling ring having an inner diameter of 20 mm and toward the tissue specimen on the glass substrate, 200 μL of a solution containing a secondary antibody was dripped and a square-wave electric field was applied for 5 minutes to the solution under conditions of applied electric field strength: 4 kV, offset voltage: 2 kV, and frequency: 1 to 30 Hz. The gap between the electrode and the solution was 4.5 mm.

The electric field conditions applied in performing the washing step after the antigen-antibody reaction of the primary antibody and the secondary antibody were as follows. After the solution containing the secondary antibody was drained by using the drain tube, 400 μL of PBS serving as a washing solution was supplied to the tissue specimen on the glass substrate by using the supply tube 12, and a square-wave electric field was applied for 30 seconds to the washing solution under conditions of applied electric field strength: 4 kV, offset voltage: 2 kV, and frequency: 1 to 30 Hz. The gap between the electrode and the washing solution was 6 mm. Subsequently, the washing solution was drained by using the drain tube. Note that in this washing step, the washing time was 30 seconds and the number of times of the washing was 2, which was sufficient.

In the present invention, the time required to perform immunohistochemical staining is 22.5 minutes, which is shortened to about one seventh of the time required in Comparative Example 4 (151 minutes). It can be understood that, despite of this, the results of immunohistochemical staining of Example 1 according to the present invention shown in FIG. 15(b) are as clear as those of Comparative Example 4 shown in FIG. 15(a).

Example 2

In Example 2, immunohistochemical staining was performed on a lymph node tissue by using an automatic electric field immunohistochemical staining apparatus according to the present invention. The basic protocol was as shown in [Table 1] above. A photomicrograph of the results of immunohistochemical staining of Example 2 is shown in FIG. 16(b). FIG. 16(a) shows an example of immunohistochemical staining conducted as Comparative Example 5 and shows a photomicrograph of results obtained thereby. In Comparative Example 5, immunohistochemical staining was performed as in the basic protocol shown in [Table 1] above except that no electric field was applied during the antigen-antibody reactions and washing with PBS and thus the solutions and the washing solutions were unstirred.

The primary antibody and the secondary antibody used in immunohistochemical staining in Example 2 and the amounts thereof, the amount of the washing solution, and the inner diameter of the water-repelling ring are shown in [Table 4] below.

TABLE 4

| | Tissue | Lymph node |
|---|---|---|
| Antibody | | Anti-CD20 Antibody (B-cell) |
| | Primary antibody | IR series diluted antibodies for tissue staining produced by DAKO |
| | Secondary antibody | Envision produced by DAKO |
| Amount | Antibody | 200 μL |
| | Washing solution | 400 μL |
| | Diameter of water-repelling ring | 20 mm |

In Example 2, the electric field conditions applied in performing the antigen-antibody reaction of the primary antibody and the antigen were as follows. Into a water-repelling ring having an inner diameter of 20 mm and toward a tissue specimen on a glass substrate, 200 μL of a solution containing a primary antibody was dripped, and a square-wave electric field was applied for 5 minutes to the solution under conditions of applied electric field strength: 4 kV, offset voltage: 2 kV, and frequency: 10 Hz. The gap between the electrode and the solution was 4.5 mm.

The electric field conditions applied in performing the washing step after the antigen-antibody reaction of the primary antibody and the antigen were as follows. After the solution containing the primary antibody was drained by using a drain tube, 400 μL of PBS serving as a washing solution was supplied to the tissue specimen on the glass substrate by using the supply tube 12, and a square-wave electric field was applied for 30 seconds to the washing solution under conditions of applied electric field strength: 4 kV, offset voltage: 2 kV, and frequency: 10 Hz. The gap between the electrode and the washing solution was 6 mm. Subsequently, the washing solution was drained by using the drain tube. Note that, in the washing step, the washing time was 30 seconds and the number of times of the washing was 1, which was sufficient.

The electric field conditions applied in performing the antigen-antibody reaction of the primary antibody and the secondary antibody were as follows. Into a water-repelling ring having an inner diameter of 20 mm and toward the tissue specimen on the glass substrate, 200 μL of a solution containing a secondary antibody was dripped, and a square-wave electric field was applied for 5 minutes to this solution under conditions of applied electric field strength: 4 kV, offset voltage: 2 kV, and frequency: 10 Hz. The gap between the electrode and the solution was 4.5 mm.

The electric field conditions applied in performing the antigen-antibody reaction of the primary antibody and the secondary antibody were as follows. After the solution containing the secondary antibody was drained by using the drain tube, 400 μL of PBS serving as a washing solution was supplied to the tissue specimen on the glass substrate by using the supply tube 12, and a square-wave electric field was applied for 30 seconds to the washing solution under conditions of applied electric field strength: 4 kV, offset voltage: 2 kV, and frequency: 10 Hz. The gap between the electrode and the washing solution was 6 mm. Subsequently, the washing solution was drained by using the drain tube. Note that, in this washing step, the washing time was 30 seconds, and the number of times of the washing was 1, which was sufficient.

It is understood that, in Example 2, the results of immunohistochemical staining according to the present invention shown in FIG. 16(b) are clearer than those of Comparative Example 5 shown in FIG. 16(a). Note that in Example 2, activation of the antigen by application of an electric field is not performed.

Embodiments of the present invention have been described heretofore in detail as examples but these embodiments disclosed are those which the applicant believes to be the best mode and do not limit the present invention. The present invention can be subject to various design modifications without deviating from the matter described in Claims.

For example, in implementing the present invention, a blocking step for suppressing non-specific reaction with an antigen and improving the stainability for immunohistochemical staining is not necessary; however, immunohistochemical staining itself is not adversely affected by performing a blocking step despite this. Moreover, in the case where a highly reactive antibody is used, such as CK or CD20, there may be cases where the step of activating an antigen is not necessary to be performed. Moreover, as discussed above, the present invention makes it possible to apply immunohistochemical staining to intraoperative rapid pathological diagnosis under time constraints. Furthermore, it becomes possible to perform immunohistochemical staining with a diluted antibody reagent, in other words, economical use of reagents. The present invention is not only applicable to intraoperative rapid diagnosis using frozen slices and immunohistochemical staining diagnosis using paraffin-embedded slices, but also can contribute to acceleration and automation of nucleic acid hybridization, other antigen-antibody reactions, etc.

Furthermore, although the embodiments described above have such a structure that a series of reactions constituting immunohistochemical staining are performed by transporting a sample mounting unit, the present invention is not limited to this. The present invention can be configured such that a solution supply unit, an electric field stirring unit, and a washing unit are transported to perform a series of reactions constituting the immunohistochemical staining while leaving a sample mounting unit fixed. In such a configuration, the present invention has an advantage that the solution or the like dripped onto the substrate in the sample mounting unit never spills.

What is claimed is:

1. An automatic electric field immunohistochemical staining apparatus that accelerates and automates, by a stirring phenomenon based on electric field application, a series of reactions constituting immunohistochemical staining for detecting an antigen in a subject tissue specimen by using a predetermined primary antibody, the apparatus comprising:
    a sample mounting unit having a stage on which a substrate with the tissue specimen fixed thereto is mounted;
    a solution supply unit provided with a container portion that contains a first solution containing the primary antibody and a dripping member that drips the solution from the container portion onto the tissue specimen on the substrate;
    an electric field stirring unit provided with a first electrode having (i) a plate shape which has a penetrating hole therethrough or (ii) a ring shape with its penetrating hole through its center, wherein the electric field stirring unit is located in the apparatus so that the electric field stirring unit stirs the solution on the tissue specimen fixed to the substrate when the substrate with the tissue specimen fixed thereto is positioned directly below the first electrode of the electric field stirring unit; and
    a washing unit provided with a drain tube that drains the solution dripped onto the tissue specimen on the substrate.

2. The automatic electric field immunohistochemical staining apparatus according to claim 1, wherein the sample mounting unit can be transported back and forth or right and left.

3. The automatic electric field immunohistochemical staining apparatus according to claim 1, wherein a second electrode is disposed inside the sample mounting unit.

4. The automatic electric field immunohistochemical staining apparatus according to claim 3, wherein the second electrode can be transported back and forth or right and left.

5. The automatic electric field immunohistochemical staining apparatus according to claim 3, wherein the second electrode is disposed inside the stage.

6. The automatic electric field immunohistochemical staining apparatus according to claim 1, wherein the container portion is provided in a cassette body.

7. The automatic electric field immunohistochemical staining apparatus according to claim 1, wherein the drain tube can be moved in and out of the penetrating hole in the first electrode.

8. The automatic electric field immunohistochemical staining apparatus according to claim 2,
    wherein when the sample mounting unit is transported and the substrate with the tissue specimen fixed thereto is positioned directly below the container portion of the solution supply unit, the solution is dripped onto the tissue specimen.

9. The automatic electric field immunohistochemical staining apparatus according to claim 8,
    wherein when the sample mounting unit is transported and the substrate with the tissue specimen fixed thereto is positioned directly below the first electrode of the electric field stirring unit after dripping of the solution, an electric field is applied to the solution dripped onto the tissue specimen and the solution is stirred to perform the reaction.

10. The automatic electric field immunohistochemical staining apparatus according to claim 9,
    wherein the solution is drained by using the drain tube of the washing unit from the tissue specimen on which the reaction has been performed.

11. The automatic electric field immunohistochemical staining apparatus according to claim 10,
    wherein the washing unit is provided with a supply tube that supplies a washing solution for washing the tissue specimen to the tissue specimen on the substrate, and
    the washing solution is supplied through the supply tube to the tissue specimen on which the reaction has been performed.

12. The automatic electric field immunohistochemical staining apparatus according to claim 11, wherein the supply tube can be moved in and out of the penetrating hole in the first electrode.

13. The automatic electric field immunohistochemical staining apparatus according to claim 1,
    wherein a plurality of divided regions are formed in the substrate and the tissue specimen can be mounted on each of these regions and fixed thereto; and
    a plurality of the first electrodes are provided to correspond to the regions.

14. The automatic electric field immunohistochemical staining apparatus according to claim 1,
    wherein a positive control or a negative control which serves as an indicator of whether or not an antigen-antibody reaction of the antigen and the antibody has been performed is fixed to the substrate.

15. The automatic electric field immunohistochemical staining apparatus according to claim 1,
    wherein protrusions protrude from the first electrode symmetrically about the penetrating hole as a center point.

16. An automatic electric field immunohistochemical staining method performed by using the automatic electric field immunohistochemical staining apparatus according to claim 1, the method comprising the steps of:
    dripping the first solution containing the primary antibody that reacts with the antigen onto the tissue specimen, and applying the electric field to the first solution to stir the first solution and to perform an antigen-antibody reaction of the antigen and the primary antibody.

17. The automatic electric field immunohistochemical staining method according to claim 16, the method comprising the steps of:
aspirating and draining the first solution after the antigen-antibody reaction of the antigen and the primary antibody.

18. The automatic electric field immunohistochemical staining method according to claim 17, the method comprising the steps of:
dripping a second solution containing a secondary antibody that reacts with the primary antibody onto the tissue specimen after aspirating and draining the first solution, and applying the electric field to the second solution to stir the second solution and to perform an antigen-antibody reaction of the primary antibody and the secondary antibody.

19. The automatic electric field immunohistochemical staining method according to claim 18, comprising the steps of:
aspirating and draining the second solution after the antigen-antibody reaction of the primary antibody and the secondary antibody.

20. The automatic electric field immunohistochemical staining method according to claim 19,
wherein the steps from performing the antigen-antibody reaction of the antigen and the primary antibody to aspirating and draining the second solution are automated.

21. The automatic electric field immunohistochemical staining method according to claim 20,
wherein the washing unit includes a supply tube that supplies a washing solution for washing the tissue specimen to the tissue specimen on the substrate,
after aspirating and draining the first solution and before performing the antigen-antibody reaction of the primary antibody and the secondary antibody, the washing solution is supplied by the supply tube to the tissue specimen and the electric field is applied to the washing solution to stir the washing solution and wash the tissue specimen, and
after aspirating and draining the second solution, the washing solution is supplied by the supply tube to the tissue specimen and the electric field is applied to the washing solution to stir the washing solution and wash the tissue specimen.

22. The automatic electric field immunohistochemical staining method according to claim 21,
wherein
the supply tube can be moved in and out of the penetrating hole in the first electrode.

23. The automatic electric field immunohistochemical staining method according to claim 16,
wherein a plurality of divided regions are formed in the substrate and the tissue specimen can be mounted on each of these regions and fixed thereto, and
a plurality of the first electrodes are provided to correspond to the regions.

24. The automatic electric field immunohistochemical staining method according to claim 16,
wherein a positive control or a negative control which serves as an indicator of whether or not the antigen-antibody reaction of the antigen and the antibody has been performed is fixed to the substrate.

* * * * *